United States Patent [19]
Reiley et al.

[11] Patent Number: 5,827,289
[45] Date of Patent: Oct. 27, 1998

[54] INFLATABLE DEVICE FOR USE IN SURGICAL PROTOCOLS RELATING TO TREATMENT OF FRACTURED OR DISEASED BONES

[76] Inventors: Mark A. Reiley, 304 Pala Ave., Piedmont, Calif. 94611; Arie Scholten, 4175 Tamayo St., Freemont, Calif. 94536; Karen D. Talmadge, 2320 Bryant St., Palo Alto, Calif. 94301

[21] Appl. No.: 659,678

[22] Filed: Jun. 5, 1996

Related U.S. Application Data

[63] Continuation-in-part of Ser. No. 485,394, Jun. 7, 1995, abandoned, which is a continuation-in-part of Ser. No. 188,224, Jan. 26, 1994, abandoned.

[51] Int. Cl.⁶ .................................................. A61B 17/56
[52] U.S. Cl. ........................ 606/86; 606/60; 606/191; 606/192
[58] Field of Search .................. 606/60, 62, 63, 606/86, 87, 89, 191, 192

[56] References Cited

U.S. PATENT DOCUMENTS

| | | | |
|---|---|---|---|
| 1,965,653 | 7/1934 | Kennedy | 128/344 |
| 3,091,237 | 5/1963 | Skinner | 128/60 |
| 3,112,743 | 12/1963 | Cochran et al. | 128/92 |

(List continued on next page.)

FOREIGN PATENT DOCUMENTS

| | | |
|---|---|---|
| 439636 | 5/1912 | France . |
| 3736604 | 5/1989 | Germany . |
| 9001858 | 3/1992 | Netherlands . |
| 906530 | 2/1982 | Russian Federation . |
| 1148610 | 4/1985 | Russian Federation . |
| 512 456 | 9/1939 | United Kingdom . |

OTHER PUBLICATIONS

Riggs et al. *New England Journal of Medicine* (1986) 1676–1686. Medical Progress, Involutional Osteoporosis.
Cohen et al. *The Orthopedic Clinics of North America* (1990) 21:143–152. Fractures of the Osteoporotic Spine, Pathologic Fractures in Betabolic Bone Disease.
Silverman Bone (1992) 13:S27–S31. The Clinical Consequences of Vertebral Compression Fracture.
Melton et al. *Journal of Bone and Mineral Research* (1992) 7:1005–1010. Perspective: How Many Women Have Osteoporosis.

(List continued on next page.)

*Primary Examiner*—Michael Powell Buiz
*Assistant Examiner*—Daphna Shai
*Attorney, Agent, or Firm*—Ryan, Maki, Mann & Hohenfeldt

[57] ABSTRACT

A balloon for use in compressing cancellous bone and marrow (also known as medullary bone or trabecular bone) against the inner cortex of bones whether the bones are fractured or not. The balloon comprises an inflatable, non-expandable balloon body for insertion into said bone. The body has a shape and size to compress at least a portion of the cancellous bone to form a cavity in the cancellous bone and to restore the original position of the outer cortical bone, if fractured or collapsed. The balloon is prevented from applying excessive pressure to the outer cortical bone. The wall or walls of the balloon are such that proper inflation the balloon body is achieved to provide for optimum compression of all the bone marrow. The balloon is able to be folded so that it can be inserted quickly into a bone. The balloon can be made to have a suction catheter. It can also be coated with therapeutic substances. The main purpose of the balloon is the forming or enlarging of a cavity or passage in a bone, especially in, but not limited to, vertebral bodies. Another important purpose is to deliver therapeutic substances to bone in an improved way.

10 Claims, 13 Drawing Sheets

U.S. PATENT DOCUMENTS

| | | | |
|---|---|---|---|
| 3,648,294 | 3/1972 | Shahrestani | 128/92 |
| 3,766,924 | 10/1973 | Pidgeon . | |
| 3,800,788 | 4/1974 | White . | |
| 3,850,176 | 11/1974 | Gottschalk . | |
| 3,875,595 | 4/1975 | Froning | 128/92 |
| 3,889,665 | 6/1975 | Ling et al. | 128/92 |
| 4,274,163 | 6/1981 | Malcom et al. | 128/92 |
| 4,313,434 | 2/1982 | Segal | 128/92 |
| 4,399,814 | 8/1983 | Pratt, Jr. et al. | 128/92 |
| 4,462,394 | 7/1984 | Jacobs | 128/92 |
| 4,466,435 | 8/1984 | Murray | 128/303 |
| 4,467,479 | 8/1984 | Brody . | |
| 4,488,549 | 12/1984 | Lee et al. | 128/303 |
| 4,562,598 | 1/1986 | Kranz | 623/18 |
| 4,595,006 | 6/1986 | Burke et al. . | |
| 4,625,722 | 12/1986 | Murray | 128/92 |
| 4,627,434 | 12/1986 | Murray | 128/303 |
| 4,628,945 | 12/1986 | Johnson, Jr. | 128/80 |
| 4,697,584 | 10/1987 | Haynes | 128/92 |
| 4,706,670 | 11/1987 | Andersen et al. | 128/344 |
| 4,714,478 | 12/1987 | Fischer | 623/23 |
| 4,772,287 | 9/1988 | Ray et al. | 623/17 |
| 4,888,022 | 12/1989 | Huebsch . | |
| 4,888,024 | 12/1989 | Powlan . | |
| 4,892,550 | 1/1990 | Huebsch | 623/22 |
| 4,896,662 | 1/1990 | Noble . | |
| 4,932,975 | 6/1990 | Main et al. . | |
| 4,969,888 | 11/1990 | Scholten et al. | 606/94 |
| 5,002,576 | 3/1991 | Fuhrmann et al. . | |
| 5,053,035 | 10/1991 | McLaren | 606/67 |
| 5,071,435 | 12/1991 | Fuchs et al. . | |
| 5,102,413 | 4/1992 | Poddar | 606/62 |
| 5,108,404 | 4/1992 | Scholten et al. . | |
| 5,147,366 | 9/1992 | Arroyo et al. | 606/94 |
| 5,163,989 | 11/1992 | Campbell et al. | 65/110 |
| 5,176,683 | 1/1993 | Kimsey et al. | 606/86 |
| 5,176,692 | 1/1993 | Wilk et al. | 606/151 |
| 5,213,576 | 5/1993 | Abiuso et al. . | |
| 5,303,718 | 4/1994 | Krajicek . | |
| 5,330,429 | 7/1994 | Noguchi et al. | 604/96 |
| 5,331,975 | 7/1994 | Bonutti | 606/192 |
| 5,361,752 | 11/1994 | Moll et al. | 128/20 |
| 5,383,932 | 1/1995 | Wison et al. . | |
| 5,423,850 | 6/1995 | Berger . | |
| 5,441,538 | 8/1995 | Bonutti . | |
| 5,454,365 | 10/1995 | Bonutti . | |
| 5,468,245 | 11/1995 | Vargas, III . | |
| 5,480,400 | 1/1996 | Berger . | |
| 5,514,143 | 5/1996 | Bonutti et al. . | |
| 5,514,153 | 5/1996 | Bonutti . | |
| 5,522,790 | 6/1996 | Moll et al. . | |
| 5,522,846 | 6/1996 | Bonutti . | |
| 5,527,343 | 6/1996 | Bonutti . | |
| 5,527,624 | 6/1996 | Higgins et al. . | |
| 5,531,856 | 7/1996 | Moll et al. . | |
| 5,540,711 | 7/1996 | Kieturakis et al. . | |
| 5,545,222 | 8/1996 | Bonutti . | |
| 5,549,679 | 8/1996 | Kuslich . | |
| 5,562,736 | 10/1996 | Ray et al. . | |
| 5,571,109 | 11/1996 | Bertagnoli . | |
| 5,571,189 | 11/1996 | Kuslich . | |

OTHER PUBLICATIONS

K. Harrington *The Journal of Bone and Jount Surgery* (1972) 54A:1665–1676. The Use of Methylmethacrylate as an Adjunct in the Internal Fixation of Malignant Neoplastic Fractures.

Instructions entitled "Exeter Pressurizer system", by Howmedica Inc., Orthopaedics Division, 1979, 2 pages.

B. Lawrence Riggs, M.D. et al. "Medical Progress, Involutional Osteoporosis", The New England Journal of Medicine, Jun. 26, 1986, pp. 1676–1686.

Lawrence D. Cohen, M.D., "Fractures of the Osteoporotic Spine", Pathologic Fractures in Betabolic Bone Disease, the Orthopedic Clinics of North America, vol. 21:1, Jan. 1990, pp. 143–152.

S. L. Silverman, "The Clinical Consequences of Vetebral Compression Fracture", Bone, 13, S27–S31 (1992).

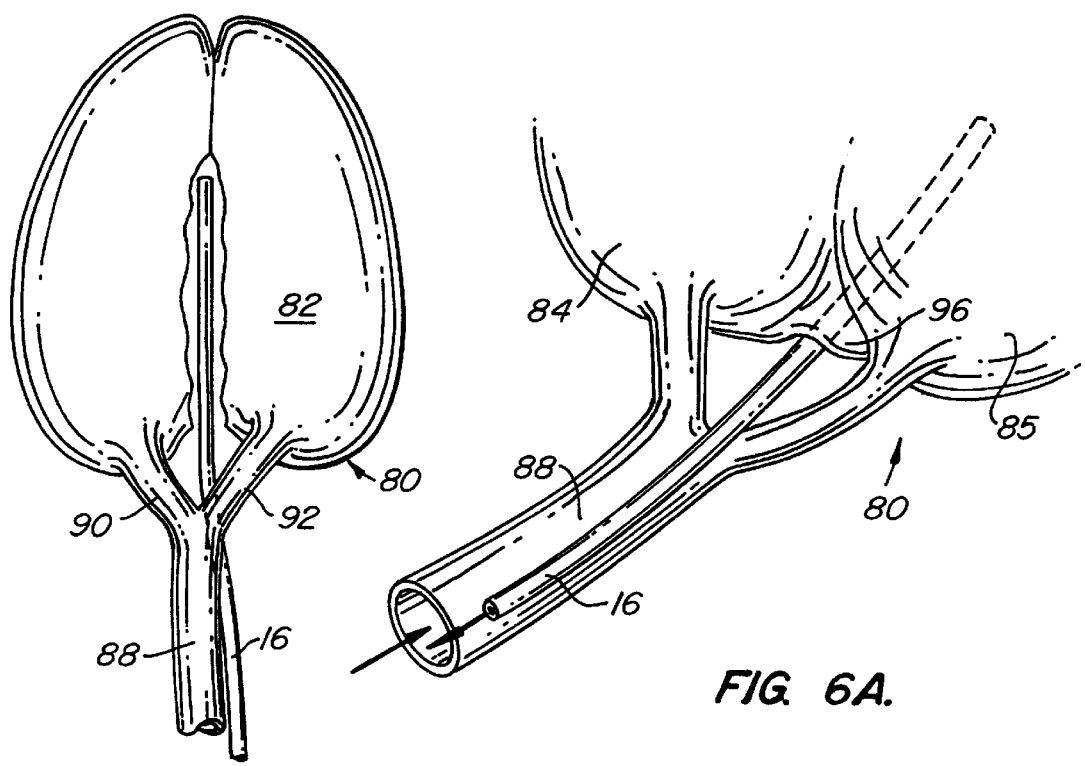
FIG. 6.
FIG. 6A.
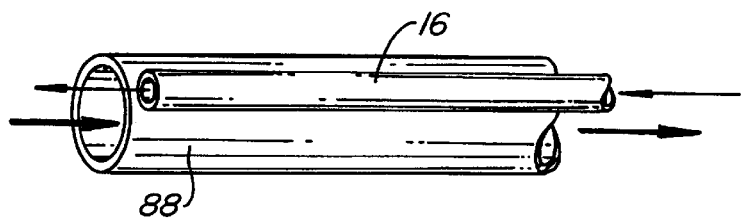
FIG. 7.
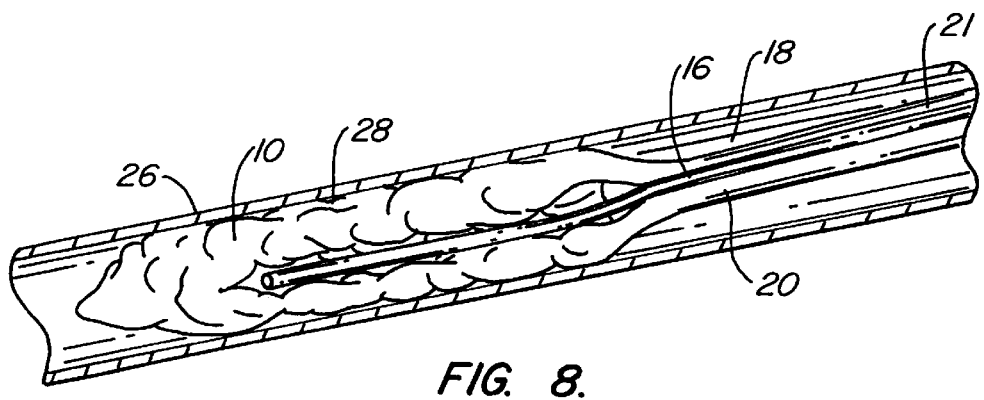
FIG. 8.

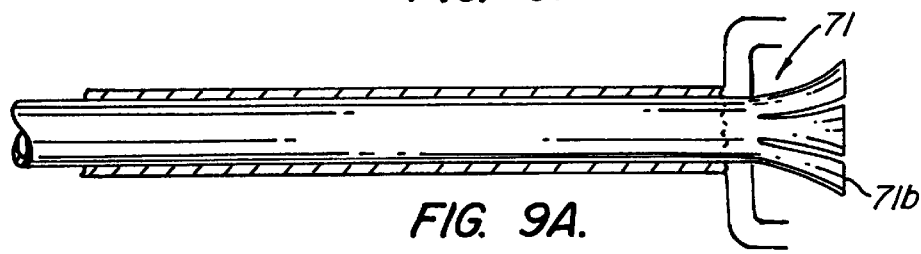
FIG. 9.
FIG. 9A.
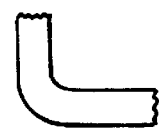
FIG. 9B.
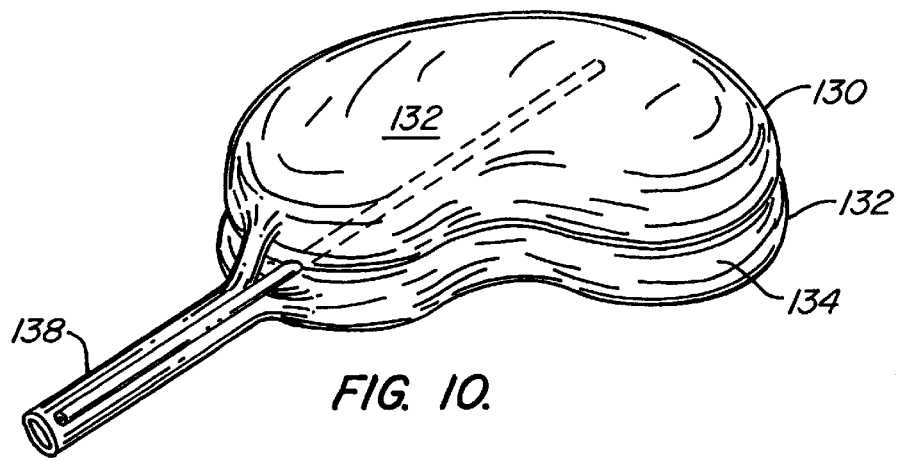
FIG. 10.
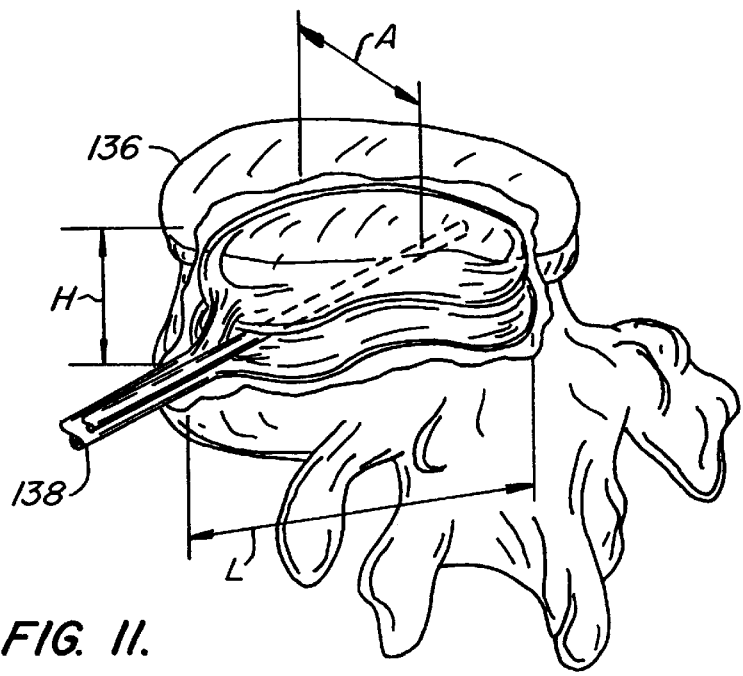
FIG. 11.

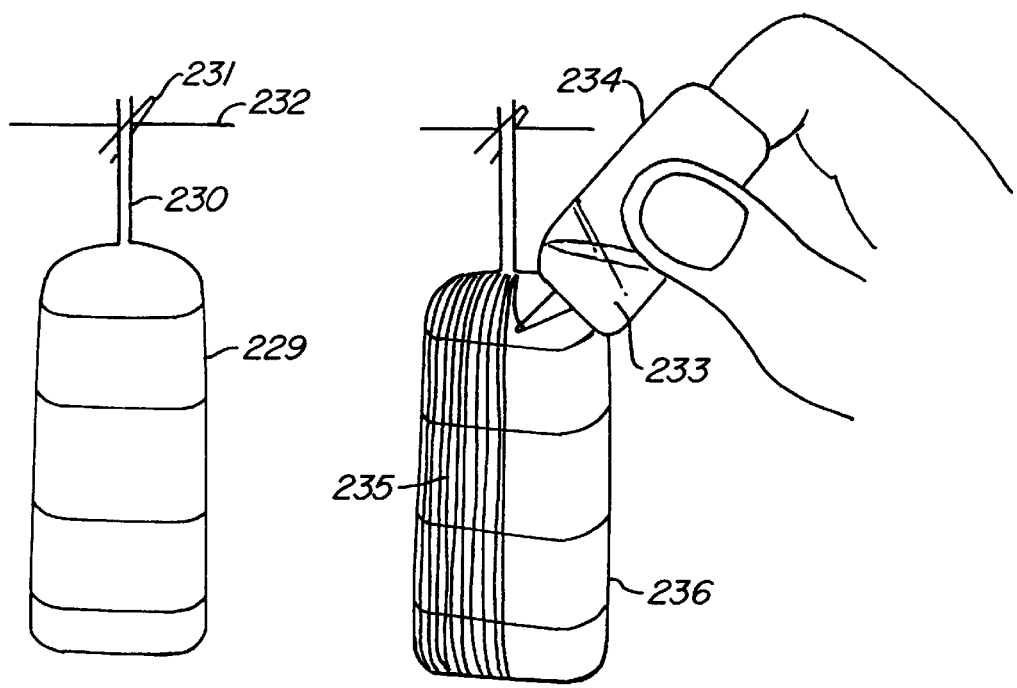
FIG. 22A.
FIG. 22B.
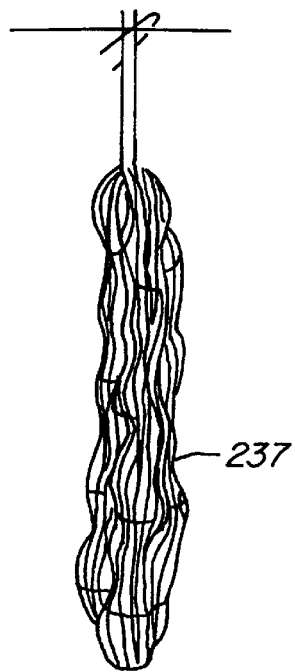
FIG. 22C.

INFLATABLE DEVICE FOR USE IN SURGICAL PROTOCOLS RELATING TO TREATMENT OF FRACTURED OR DISEASED BONES

This application is a continuation-in-part of U.S. patent application Ser. No. 08/485,394, filed Jun. 7, 1995, now abandoned, which is a continuation-in-part of U.S. patent application Ser. No. 08/188,224, filed Jan. 26, 1994 entitled, "Improved Inflatable Device For Use In Surgical Protocol Relating To Fixation Of Bone, now abandoned."

This invention relates to improvements in the surgical treatment of bone conditions of the human and other animal bone systems and, more particularly, to an inflatable balloon-like device for use in treating such bone conditions.

Osteoporosis, avascular necrosis and bone cancer are diseases of bone that predispose the bone to fracture or collapse. There are 2 million fractures each year in the United States, of which about 1.3 million are caused by osteoporosis, while avascular necrosis and bone cancers are more rare. These conditions cause bone problems that have been poorly addressed, resulting in deformities and chronic complications.

The outcome of many other orthopedic procedures to treat bone, such as open surgeries involving infected bone, poorly healing bone or bone fractured by severe trauma, can also be improved. Currently, bone is prepared to receive materials such as bone graft or bone substitutes by removing diseased or injured bone using standard tools, usually made of metal. Gaps between the patient's remaining bone and the inserted materials delay or prevent healing.

Therapeutic substances like antibiotics and bone growth factors have not been applied to bone in a way that optimizes and maintains their contact with the desired area of bone. Antibiotics, bone growth factors and other drugs can prevent complications and hasten repair. They are currently placed as dry powders or liquids around the treated bone, or else are formulated into a gel or a degradable plastic polymer and inserted into areas with defects (holes in the bone). Delivered in this manner, they can be washed away by blood or other fluids, either immediately or as their carrier degrades. Also, the amount of therapeutic substance delivered in a gel or polymer can be limited by the space provided by the defect.

BACKGROUND OF THE INVENTION

In U.S. Pat. Nos. 4,969,888 and 5,108,404, an apparatus and method are disclosed for the fixation of fractures or other conditions of human and other animal bone systems, both osteoporotic and non-osteoporotic. The apparatus and method are especially suitable for, but not limited to, use in the fixation of vertebral body compression fractures, Colles fractures and fractures of the proximal humerus.

The method disclosed in these two patents includes a series of steps in which a surgeon or health care provider can perform to form a cavity in fractured or pathological bone (including but not limited to osteoporotic bone, osteoporotic fractured metaphyseal and epiphyseal bone, osteoporotic vertebral bodies, fractured osteoporotic vertebral bodies, fractures of vertebral bodies due to tumors especially round cell tumors, avascular necrosis of the epiphyses of long bones, especially avascular necrosis of the proximal femur, distal femur and proximal humerus and defects arising from endocrine conditions).

The method further includes an incision in the skin (usually one incision, but a second small incision may also be required if a suction egress is used) followed by the placement of a guide pin which is passed through the soft tissue down to and into the bone.

The method further includes drilling the bone to be treated to form a cavity or passage in the bone, and inserting an inflatable balloon-like device into the cavity or passage. Inflation of the inflatable device causes a compacting of the cancellous bone and bone marrow against the inner surface of the cortical wall of the bone to further enlarge the cavity or passage. The inflatable device is then deflated and then is completely removed from the bone. A smaller inflatable device (a starter balloon) can be used initially, if needed, to initiate the compacting of the bone marrow and to commence the formation of the cavity or passage in the cancellous bone and marrow. After this has occurred, a larger, inflatable device is inserted into the cavity or passage to further compact the bone marrow in all directions.

A flowable biocompatible filling material, such as methylmethacrylate cement or a synthetic bone substitute, is then directed into the cavity or passage and allowed to set to a hardened condition to provide structural support for the bone. Following this latter step, the insertion instruments are removed from the body and the incision in the skin is covered with a bandage.

While the apparatus and method of the above patents provide an adequate protocol for the fixation of bone, it has been found that the compacting of the bone marrow and/or the trabecular bone and/or cancellous bone against the inner surface of the cortical wall of the bone to be treated can be significantly improved with the use of inflatable devices that incorporate additional engineering features not heretofore described and not properly controlled with prior inflatable devices in such patents. It has also been found that therapeutic substances can be delivered with the apparatus and methods of the above patents in an unexpected way. It has been additionally found that the apparatus and methods of the above patents can be adapted in ways not previously described to improve open surgeries to fix, fuse or remove bone, as well as to deliver therapeutic substances during these surgeries. A need has therefore arisen for improvements in the shape, construction and size of inflatable devices for use with the foregoing apparatus and method, as well as for new methods, and the present invention satisfies such need.

Prior Techniques For The Manufacture Of Balloons For In-Patient Use

A review of the prior art relating to the manufacture of balloons shows that a fair amount of background information has been amassed in the formation of guiding catheters which are introduced into cardiovascular systems of patients through the brachial or femoral arteries. However, there is a scarcity of disclosures relating to inflatable devices used in bone, and none for compacting bone marrow in vertebral bodies and long bones.

In a dilatation catheter, the catheter is advanced into a patient until a balloon is properly positioned across a lesion to be treated. The balloon is inflated with a radiopaque liquid at pressures above four atmospheres to compress the plaque of the lesion to thereby dilate the lumen of the artery. The balloon can then be deflated, then removed from the artery so that the blood flow can be restored through the dilated artery.

A discussion of such catheter usage technique is found and clearly disclosed in U.S. Pat. No. 5,163,989. Other details of angioplasty catheter procedures, and details of balloons used in such procedures can be found in U.S. Pat. Nos. 4,323,071, 4,332,254, 4,439,185, 4,168,224, 4,516,672, 4,538,622, 4,554,929, and 4,616,652.

Extrusions have also been made to form prism shaped balloons using molds which require very accurate machining of the interior surface thereof to form acceptable balloons for angioplastic catheters. However, this technique of extrusion forms parting lines in the balloon product which parting lines are limiting in the sense of providing a weak wall for the balloon itself.

U.S. Pat. No. 5,163,989 discloses a mold and technique for molding dilatation catheters in which the balloon of the catheter is free of parting lines. The technique involves inflating a plastic member of tubular shape so as to press it against the inner molding surface which is heated. Inflatable devices are molded into the desired size and shape, then cooled and deflated to remove it from the mold. The patent states that, while the balloon of the present invention is especially suitable for forming prism-like balloons, it can also be used for forming balloons of a wide variety of sizes and shapes.

A particular improvement in the catheter art with respect to this patent, namely U.S. Pat. No. 4,706,670, is the use of a coaxial catheter with inner and outer tubing formed and reinforced by continuous helical filaments. Such filaments cross each other causing the shaft of the balloon to become shorter in length while the moving portion of the shank becomes longer in length. By suitably balancing the lengths and the angle of the weave of the balloon and moving portions of the filaments, changes in length can be made to offset each other. Thus, the position of the inner and outer tubing can be adjusted as needed to keep the balloon in a desired position in the blood vessel.

Other disclosures relating to the insertion of inflatable devices for treating the skeleton of patients include the following:

U.S. Pat. No. 4,313,434 relates to the fixation of a long bone by inserting a deflated flexible bladder into a medullary cavity, inflating the balloon bladder, sealing the interior of the long bone until healing has occurred, then removing the bladder and filling the opening through which the bladder emerges from the long bone.

U.S. Pat. No. 5,102,413 discloses the way in which an inflatable bladder is used to anchor a metal rod for the fixation of a fractured long bone.

Other references which disclose the use of balloons and cement for anchoring of a prosthesis include U.S. Pat. Nos. 5,147,366, 4,892,550, 4,697,584, 4,562,598, and 4,399,814.

A Dutch patent, NL 901858, discloses a means for fracture repair with a cement-impregnated bag which is inflated into a preformed cavity and allowed to harden.

It can be concluded from the foregoing review of the prior art that there is little or no substantive information on inflatable devices used to create cavities in bone. It does not teach the shape of the balloon which creates a cavity that best supports the bone when appropriately filled. It does not teach how to prevent balloons from being spherical when inflated, when this is desired. Current medical balloons can compress bone but are too small and generally have the wrong configuration and are generally not strong enough to accomplish adequate cavity formation in either the vertebral bodies or long bones of the body.

U.S. Pat. Nos. 4,969,888 and 5,108,404 disclose a checker-shaped balloon for compressing cancellous bone, but does not provide information on how this balloon remains in its shape when inflated. It also does not provide methods to deliver an enhanced supply of therapeutic agent.

U.S. Pat. No. 4,892,550 describes an elastic balloon for anchoring a metal prosthesis inside of a bone. U.S. Pat. No. 4,313,434 describes a deflatable bladder to substitute for metal rods which are placed inside the intramedullary cavity of fractured long bones (thigh, leg and arm) to keep them together while they heal.

Thus, the need continues for an improved inflatable device and methods for use with fractured and/or pathological bones.

SUMMARY OF THE INVENTION

The present invention is directed to a balloon-like inflatable device or balloon for use in carrying out the apparatus and method of the above-mentioned patents 4,969,888 and 5,108,404, and to new methods for using these devices, and to new uses of the methods and devices. Such inflatable devices, hereinafter sometimes referred to as balloons, have shapes for compressing cancellous bone and marrow (also known as medullary bone or trabecular bone) against the inner cortex of bones whether the bones are fractured or not.

In particular, the present invention is directed to a balloon for use in treating a bone predisposed to fracture or to collapse. The balloon comprises an inflatable, non-expandable balloon body for insertion into said bone. The body has a predetermined shape and size when substantially inflated sufficient to compress at least a portion of the inner cancellous bone to create a cavity in the cancellous bone and to restore the original position of the outer cortical bone, if fractured or collapsed. The balloon body is restrained to create said predetermined shape and size so that the fully inflated balloon body is prevented from applying substantial pressure to the inner surface of the outer cortical bone if said bone is unfractured or uncollapsed. Substantial pressure is defined herein as pressure sufficient to displace the cortical cone beyond its normal configuration.

In addition to the shape of the inflatable device itself, another aspect of importance is the construction of the wall or walls of the balloon such that proper inflation the balloon body is achieved to provide for optimum compression of all the bone marrow. The material of the balloon is also desirably chosen so as to be able to fold the balloon so that it can be inserted quickly and easily into a bone using a guide pin and a canula, yet can also withstand high pressures when inflated. The balloon can also include optional ridges or indentations which are left in the cavity after the balloon has been removed, to enhance the stability of the filler. Also, the inflatable device can be made to have an optional, built-in suction catheter. This is used to remove any fat or fluid extruded from the bone during balloon inflation in the bone. Also, the balloon body can be protected from puncture by the cortical bone or canula by being covered while inside the canula with an optional protective sleeve of suitable material, such as Kevlar or PET or other polymer or substance that can protect the balloon. A main purpose of the inflatable device, therefore, is the forming or enlarging of a cavity or passage in a bone, especially in, but not limited to, vertebral bodies.

In one aspect, the invention provides an improved balloon-like inflatable device for use in carrying out a surgical protocol of cavity formation in bones to enhance the efficiency of the protocol, to minimize the time prior to performing the surgery for which the protocol is designed and to improve the clinical outcome. These balloons approximate the inner shape of the bone they are inside of in order to maximally compress cancellous bone. They have additional design elements to achieve specific clinical goals. Preferably, they are made of inelastic material and kept in their defined configurations when inflated, by various restraints, including (but not limited to) use of inelastic materials in the balloon body, seams in the balloon body created by bonding or fusing separate pieces of material together, or by fusing or bonding together opposing sides of the balloon body, woven material bonded inside or outside the balloon body, strings or bands placed at selected points in the balloon body, and stacking balloons of similar or different sizes or shapes on top of each other by gluing or by heat fusing them together. Optional ridges or indentations created by the foregoing structures, or added on by bonding additional material, increases stability of the filler. Optional suction devices, preferably placed so that if at least one hole is in the lowest point of the cavity being formed, will allow the cavity to be cleaned before filling.

In another aspect, the invention provides new uses for these balloons, and new methods for their use. Balloons can be used to deliver therapeutic substances by coating the balloons with the therapeutic substance before inserting the balloon into bone. When coated balloons are inflated in bone, the therapeutic substances are pressed into the cancellous bone while that bone is being compressed by the balloon. This allows desired amounts of the therapeutic substance to be delivered directly to the site of therapy in a manner that is maintained over time. The balloons can also be used during minimally invasive or open surgeries to provide an improved space for orthopedic implants, bone graft, bone substitutes, acrylic cements, bone fillers, bone growth factors, chemotherapeutic agents, antibiotics or other drugs. The agents inside the bone can be intended to treat the bone itself or to serve as a reservoir of drug for a structure nearby, such as an osteosarcoma.

In yet another aspect of the invention, the balloons can be used to temporarily provide structural support for a fractured or diseased bone. In this embodiment, the fractured or diseased bone can be treated by inflating the balloon at the treatment site and leaving it in place until the surrounding cortical bone heals. In other words, the balloon will take the place of the biocompatible filling material used in previous methods to support the fractured or diseased bone. The invention will include a mechanism for sealing the inflated balloon outside of the bone cavity, but within the patient. The sealing mechanism can include a metal or plastic clip, a check valve activated by unscrewing the inflation tube, a plug for sealing the inner passage of the balloon or the like. Similar to previous embodiments, the balloon will be delivered into the bone and inflated to compress the inner cancellous bone and create a cavity therein. The inflated balloon will then be sealed, e.g., by inserting a plug within the inflation opening, the inflation tube will be removed from the patient, and the percutaneous incision will be closed. The fluid pressure within the balloon provides sufficient support for the bone to allow the bone to heal. The balloon can be left in the bone cavity in the inflated configuration for an amount of time necessary for the outer cortical bone to completely or at least partially heal, usually about 1 day to 3 months and preferably about 6–8 weeks. In this aspect of the invention, the balloon is providing at least four functions: (1) realigning the bones; (2) eliminating or at least reducing diseased inner cancellous bone; (3) strengthening the outer cortical bone by providing additional calcium from the compressed inner cancellous bone which is incorporated into the outer cortical bone as it heals; and (4) acting as an internal cast while the cortical bone heals.

After the cortical bone has healed, the surgeon can access the balloon through the same or another percutaneous incision to deflate the balloon by removing the clip, plug or, in the case of a check valve, by screwing the inflation tube back into the balloon. In many cases, the cortical bone will have become sufficiently strengthened through healing with additional calcium from the compressed cancellous. In these cases, the balloon will be removed from the bone cavity. The balloon may include a coating, such as Gelfoam or an antibiotic, on its outer surface to stop bleeding, prevent infection, minimize bone growth into the balloon and/or to facilitate separation of the balloon from the bone when the balloon is deflated. If, however, the surgeon determines that the cortical bone is still too weak (e.g., through a bone density scan or other measurement), appropriate supporting material, such as acrylic cements, bone substitutes, bone fillers or bone growth factors, can be inserted into the bone cavity before removal of the balloon.

The methods of the above-mentioned patents and the improvements herein can be applied anywhere in the skeleton where there is cancellous and/or trabecular and/or medullary bone.

Among the various embodiments of the present invention are the following:

1. A doughnut (or torus) shaped balloon with an optional built-in suction catheter to remove fat and other products extruded during balloon expansion.
2. A balloon with a spherical outer shape surrounded by a ring-shaped balloon segment for body cavity formation.
3. A balloon which is kidney bean shaped in configuration. Such a balloon can be constructed in a single layer, or several layers stacked on top of each other. This embodiment can also be a square or a rectangle instead of a kidney bean.
4. A spherically shaped balloon approximating the size of the head of the femur (i.e. the proximal femoral epiphysis). Such a balloon can also be a hemisphere.
5. A balloon in the shape of a humpbacked banana or a modified pyramid shape approximating the configuration of the distal end of the radius (i.e. the distal radial epiphysis and metaphysis).
6. A balloon in the shape of a cylindrical ellipse to approximate the configuration of either the medial half or the lateral half of the proximal tibial epiphysis. Such a balloon can also be constructed to approximate the configuration of both halves of the proximal tibial epiphysis.
7. A balloon in the shape of sphere on a base to approximate the shape of the proximal humeral epiphysis and metaphysis with a plug to compress cancellous bone into the diaphysis, sealing it off. Such an embodiment can also be a cylinder.
8. A balloon in the shape of a boomerang to approximate the inside of the femoral head, neck and lesser trochanter, allowing a procedure to prevent hip fracture.
9. A balloon in the shape of a cylinder to approximate the size and shape of the inside of the proximal humerus or of the distal radius.
10. A balloon device with an optional suctional device. and
11. Protective sheaths to act as puncture guard members optionally covering each balloon inside its catheter.

The present invention, therefore, provides improved, inflatable devices for creating or enlarging a cavity or passage in a bone wherein the devices are inserted into the bone. The configuration of each device is defined by the surrounding cortical bone and adjacent internal structures, and is designed to occupy about 70–90% of the volume of the inside of the bone, although balloons that are as small as about 40% and as large as about 99% are workable for fractures. In certain cases, usually avascular necrosis, the balloon size may be as small as 10% of the cancellous bone volume of the area of bone being treated, due to the localized nature of the fracture or collapse. The fully expanded size and shape of the balloon is limited by additional material in selected portions of the balloon body whose extra thickness creates a restraint as well as by either internal or external restraints formed in the device including, but not limited to, mesh work, a winding or spooling of material laminated to portions of the balloon body, continuous or non-continuous strings across the inside held in place at specific locations by glue inside or by threading them through to the outside and seams in the balloon body created by bonding two pieces of body together or by bonding opposing sides of a body through glue or heat. Spherical portions of balloons may be restrained by using inelastic materials in the construction of the balloon body, or may be additionally restrained as just described. The material of the balloon is preferably a non-elastic material, such as polyethylene tetraphthalate (PET), Kevlar or other patented medical balloon materials. It can also be made of semi-elastic materials, such as silicone or elastic material such as latex, if appropriate restraints are incorporated. The restraints can be made of a flexible, inelastic high tensile strength material including, but not limited, to those described in U.S. Pat. No. 4,706,670. The thickness of the balloon wall is typically in the range of $2/1000$ths to $25/1000$ths of an inch, or other thicknesses that can withstand pressures of up to 250–400 psi.

One important goal of percutaneous vertebral body augmentation of the present invention is to provide a balloon which can create a cavity inside the vertebral body whose configuration is optimal for supporting the bone. Another important goal is to move the top of the vertebral body back into place to retain height where possible, however, both of these objectives must be achieved without changing the outer diameter of the sides of the vertebral body, either by fracturing the cortical wall of the vertebral body or by moving already fractured bone. This feature could push vertebral bone toward the spinal cord, a condition which is not to be desired.

The present invention satisfies these goals through the design of inflatable devices to be described. Inflating such a device compresses the calcium-containing soft cancellous bone into a thin shell that lines the inside of the hard cortical bone creating a large cavity.

At the same time, the biological components (red blood cells, bone progenitor cells) within the soft bone are pressed out and removed by rinsing during the procedure. The body recreates the shape of the inside of an unfractured vertebral body, but optimally stops at approximately 70 to 90% of the inner volume. The balloons of the present invention are inelastic, so maximally inflating them can only recreate the predetermined shape and size. However, conventional balloons become spherical when inflated. Spherical shapes will not allow the hardened bone cement to support the spine adequately, because they make single points of contact on each vertebral body surface (the equivalent of a circle inside a square, or a sphere inside a cylinder). The balloons of the present invention recreate the flat surfaces of the vertebral body by including restraints that keep the balloon in the desired shape. This maximizes the contacts between the vertebral body surfaces and the bone cement, which strengthens the spine. In addition, the volume of bone cement that fills these cavities creates a thick mantle of cement (4 mm or greater), which is required for appropriate compressive strength. Another useful feature, although not required, are ridges in the balloons which leave their imprint in the lining of compressed cancellous bone. The resulting bone cement "fingers" provide enhanced stability.

The balloons which optimally compress cancellous bone in vertebral bodies are the balloons listed as balloon types 1, 2 and 3 above. These balloons are configured to approximate the shape of the vertebral body. Since the balloon is chosen to occupy 70 to 90% of the inner volume, it will not exert undue pressure on the sides of the vertebral body, thus the vertebral body will not expand beyond its normal size (fractured or unfractured). However, since the balloon has the height of an unfractured vertebral body, it can move the top, which has collapsed, back to its original position. Any number of individual balloons can be stacked, and stacks containing any of the balloons of types 1, 2 and 3 can be mixed in shape and/or size to provide greater flexibility and/or control.

A primary goal of percutaneous proximal humeral augmentation is to create a cavity inside the proximal humerus whose configuration is optimal for supporting the proximal humerus. Another important goal is to help realign the humeral head with the shaft of the humerus when they are separated by a fracture. Both of these goals must be achieved by exerting pressure primarily on the cancellous bone, and not the cortical bone. Undue pressure against the cortical bone could conceivably cause a worsening of a shoulder fracture by causing cortical bone fractures.

The present invention satisfies these goals through the design of the inflatable devices to be described. Inflating such a device compresses the cancellous bone against the cortical walls of the epiphysis and metaphysis of the proximal humerus thereby creating a cavity. In some cases, depending on the fracture location, the balloon or inflatable device may be used to extend the cavity into the proximal part of the humeral diaphysis.

Due to the design of the "sphere on a stand" balloon (described as number 7 above), the cavity made by this balloon recreates or approximates the shape of the inside cortical wall of the proximal humerus. The approximate volume of the cavity made by the "spherical on a stand balloon" is 70 to 90% that of the proximal humeral epiphysis and metaphysis, primarily, but not necessarily exclusive of, part of the diaphysis. The shape approximates the shape of the humeral head. The "base" is designed to compress the trabecular bone into a "plug" of bone in the distal metaphysis or proximal diaphysis. This plug of bone will prevent the flow of injectable material into the shaft of the humerus, improving the clinical outcome. The sphere can also be used without a base. Alternatively, the balloon can be shaped like a fat cylinder, with one end at the top of the humeral head attached to the catheter and the other end filling the function of the plug. The cylinder can also be formed so that the diameter of the end in the humerus is greater than the diameter of the end which functions as the plug.

A primary goal of percutaneous distal radius augmentation is to create a cavity inside the distal radius whose configuration is optimal for supporting the distal radius. Another important goal is to help fine tune fracture realignment after the fracture has been partially realigned by finger traps. Both of these goals must be achieved by exerting pressure primarily on the cancellous bone and not on the cortical bone. Excessive pressure against the cortical bone could conceivably cause cortical bone fractures, thus worsening the condition.

The present invention satisfies these goals through the design of inflatable devices either already described or to be described.

The design of the "humpbacked banana", or modified pyramid design (as described as number 5 above), approximates the shape of the distal radius and therefore, the cavity made by this balloon approximates the shape of the distal radius as well. The approximate volume of the cavity to be made by this humpbacked banana shaped balloon is 70 to 90% that of the distal radial epiphysis and metaphysis primarily of, but not necessarily exclusive of, some part of the distal radial diaphysis. Inflating such a device compresses the cancellous bone against the cortical walls of the epiphysis and metaphysis of the distal radius in order to create a cavity. In some cases, depending on the fracture location, the osseous balloon or inflatable device may be used to extend the cavity into the distal part of the radial diaphysis.

A primary goal of percutaneous femoral head (or humeral head) augmentation is to create a cavity inside the femoral head (or humeral head) whose configuration is optimal for supporting the femoral head. Another important goal is to help compress avascular (or aseptic) necrotic bone or support avascular necrotic bone in the femoral head. This goal may include the realignment of avascular bone back into the position it previously occupied in the femoral head in order to improve the spherical shape of the femoral head. These goals must be achieved by exerting pressure primarily on the cancellous bone inside the femoral head.

The present invention satisfied these goals through the design of inflatable devices either already described or to be described.

The design of the spherical osseous balloon (described as balloon type 4 above) approximates the shape of the femoral head and therefore creates a cavity which approximates the shape of the femoral head as well. (It should be noted that the spherical shape of this inflatable device also approximates the shape of the humeral head and would, in fact, be appropriate for cavity formation in this osseous location as well.) Inflating such a device compresses the cancellous bone of the femoral head against its inner cortical walls in order to create a cavity. In some cases, depending upon the extent of the avascular necrosis, a smaller or larger cavity inside the femoral head will be formed. In some cases, if the area of avascular necrosis is small, a small balloon will be utilized which might create a cavity only 10 to 15% of the total volume of the femoral head. If larger areas of the femoral head are involved with the avascular necrosis, then a larger balloon would be utilized which might create a much larger cavity, approaching 80 to 90% of the volume of the femoral head.

The hemispherical balloon approximates the shape of the top half of the femoral (and humeral) head, and provides a means for compacting cancellous bone in an area of avascular necrosis or small fracture without disturbing the rest of the head. This makes it easier to do a future total joint replacement if required.

Percutaneous hip augmentation is designed to prevent hip fracture by compacting weak cancellous bone in the femur where hip fractures occur and replacing it with appropriate supporting material. A primary goal of percutaneous hip augmentation is to create a cavity inside the femoral head, femoral neck and lesser trochanter which will compress diseased cancellous bone and allow it to be replaced with appropriate supporting material, preventing hip fracture. The cavity created by the procedure usually extends from the femoral head, past the lesser trochanter by a defined amount, but generally not further. The cavity should not expand into the greater trochanter, where hip fractures do not affect the patient, because this may prevent the balloon from expanding into the lesser trochanter, where hip fractures do affect the patient. The balloon should compact the cancellous bone as fully as possible without pushing the inner cortical bone, which could cause (instead of prevent) a fracture.

The present invention satisfies these goals by providing inflatable devices to be described and which have special features, including their placement on the catheter, to orient the balloon appropriately.

A primary goal of percutaneous proximal tibial augmentation is to create a cavity inside the proximal tibia whose configuration is optimal for supporting either the medial or lateral tibial plateaus. Another important goal is to help realign the fracture fragments of tibial plateau fractures, particularly those features with fragments depressed below (or inferior to) their usual location. Both of these objectives must be achieved by exerting pressure on primarily the cancellous bone and not the cortical bone. Pressure on the cortical bone could conceivably cause worsening of the tibial plateau fracture.

The present invention satisfies these goals through the design of the inflatable devices to be described. Inflating such a device compresses the cancellous bone against the cortical walls of the medial or lateral tibial plateau in order to create a cavity.

Due to the design of the "elliptical cylinder" balloon (described as balloon type 6 above) the cavity made by this balloon recreates or approximates the shape of the cortical walls of either the medial or lateral tibial plateaus. The approximate volume of the cavity to be made by the appropriate elliptical cylindrical balloon is 50 to 90% of the proximal epiphyseal bone of either the medial half or the lateral half of the tibial.

Due to the nature of the injury, disease or other treatments, it may be preferable to treat a bone with the devices of this invention during an open surgical procedure. In addition, a goal of the percutaneous or open surgery may be to replace the diseased or injured bone with materials (such as bone fillers or certain drugs) which do not flow.

The present invention satisfies these goals through the systems and methods of this invention described below.

Other objects of the present invention will become apparent as the following specification progresses, reference being had to the accompanying drawings for an illustration of the invention.

BRIEF DESCRIPTION OF THE DRAWINGS

FIG. 6 shows an oblong-shaped balloon with a catheter extending into the central portion of the balloon;

FIG. 6A is a perspective view of the way in which a catheter is arranged relative to the inner tubes for inflating the balloon of FIG. 6;

FIG. 7 is a suction tube and a contrast injection tube for carrying out the inflation of the balloon and removal of debris caused by expansion from the balloon itself;

FIG. 8 is a vertical section through a balloon after it has been deflated and as it is being inserted into the vertebral body of a human;

FIGS. 9 and 9A are side elevational views of a canula showing how the protective sleeve or guard member expands when leaving the canula;

FIG. 9B is a vertical section through a vertebral bone into which an access hole has been drilled;

FIG. 10 is a perspective view of another embodiment of the balloon of the present invention formed in the shape of a kidney bean;

FIG. 11 is a perspective view of the vertebral bone showing the kidney shaped balloon of FIG. 10 inserted in the bone and expanded;

FIGS. 22A–C are schematic illustrations of a representative method and system for delivering a therapeutic substance to a bone according to the present invention.

DETAILED DESCRIPTION OF THE PREFERRED EMBODIMENT

Balloons For Vertebral Bodies

A first embodiment of the balloon (FIG. 1) of the present invention is broadly denoted by the numeral 10 and includes a balloon body 11 having a pair of hollow, inflatable, non-expandable parts 12 and 14 of flexible material, such as PET or Kevlar. Parts 12 and 14 have a suction tube 16 therebetween for drawing fats and other debris by suction into tube 16 for transfer to a remote disposal location. Catheter 16 has one or more suction holes so that suction may be applied to the open end of tube 16 from a suction source (not shown).

Figure 1:
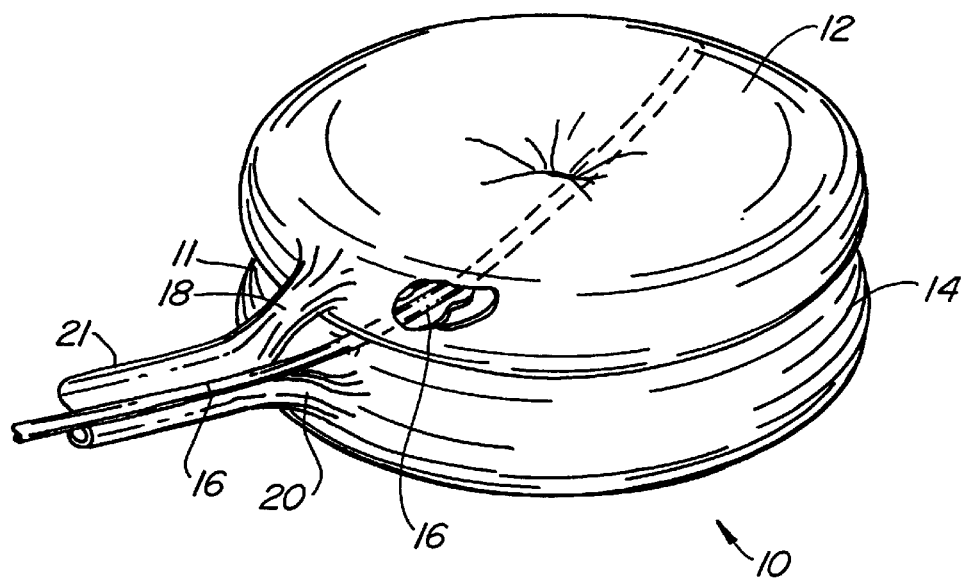
FIG. 1 is a perspective view of a first embodiment of the balloon of the present invention, the embodiment being in the shape of a stacked doughnut assembly.

The parts 12 and 14 are connected together by an adhesive which can be of any suitable type. Parts 12 and 14 are doughnut-shaped as shown in FIG. 1 and have tubes 18 and 20 which communicate with and extend away from the parts 12 and 14, respectively, to a source of inflating liquid under pressure (not shown). The liquid can be any sterile biocompatible solution. The liquid inflates the balloon 10, particularly parts 12 and 14 thereof after the balloon has been inserted in a collapsed condition (FIG. 8) into a bone to be treated, such as a vertebral bone 22 in FIG. 2. The above-mentioned U.S. Pat. Nos. 4,969,888 and 5,108,404 disclose the use of a guide pin and canula for inserting the balloon into bone to be treated when the balloon is deflated and has been inserted into a tube and driven by the catheter into the cortical bone where the balloon is inflated.

FIG. 8 shows a deflated balloon 10 being inserted through a canula 26 into bone. The balloon in canula 26 is deflated and is forced through the canula by exerting manual force on the catheter 21 which extends into a passage 28 extending into the interior of the bone. The catheter is slightly flexible but is sufficiently rigid to allow the balloon to be forced into the interior of the bone where the balloon is then inflated by directing fluid into tube 88 whose outlet ends are coupled to respective parts 12 and 14.

Figure 2:
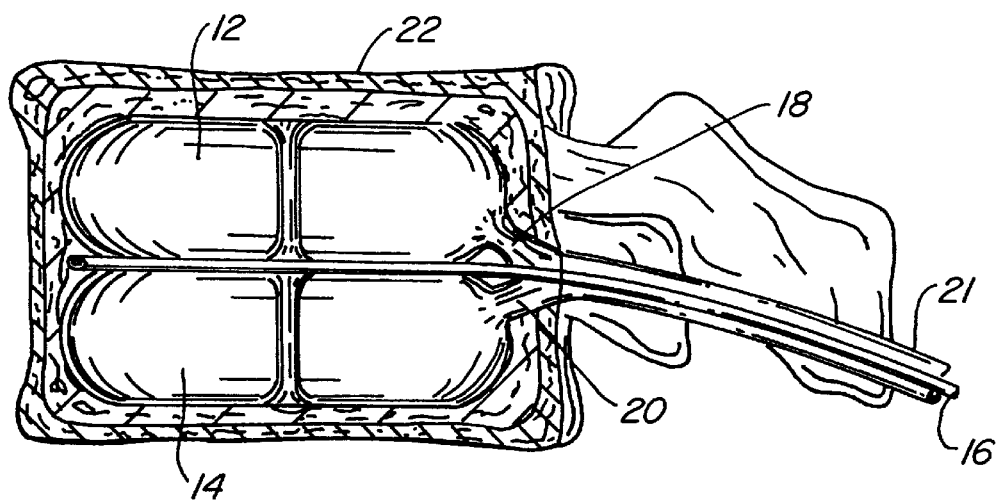
FIG. 2 is a vertical section through the balloon of FIG. 1 showing the way in which the doughnut portions of the balloon of FIG. 1, fit into a cavity of a vertebral body.

In use, balloon 10 is initially deflated and, after the bone to be filled with the balloon has been prepared to receive the balloon with drilling, the deflated balloon is forced into the bone in a collapsed condition through canula 26. The bone is shown in FIG. 2. The balloon is oriented preferably in the bone such that it allows minimum pressure to be exerted on the bone marrow and/or cancellous bone if there is no fracture or collapse of the bone. Such pressure will compress the bone marrow and/or cancellous bone against the inner wall of the cortical bone, thereby compacting the bone marrow of the bone to be treated and to further enlarge the cavity in which the bone marrow is to be replaced by a biocompatible, flowable bone material.

The balloon is then inflated to compact the bone marrow and/or cancellous bone in the cavity and, after compaction of the bone marrow and/or cancellous bone, the balloon is deflated and removed from the cavity. While inflation of the balloon and compaction occurs, fats and other debris are sucked out of the space between and around parts 12 and 14 by applying a suction force to catheter tube 16. Following this, and following the compaction of the bone marrow, the balloon is deflated and pulled out of the cavity by applying a manual pulling force to the catheter tube 21.

Figure 4:
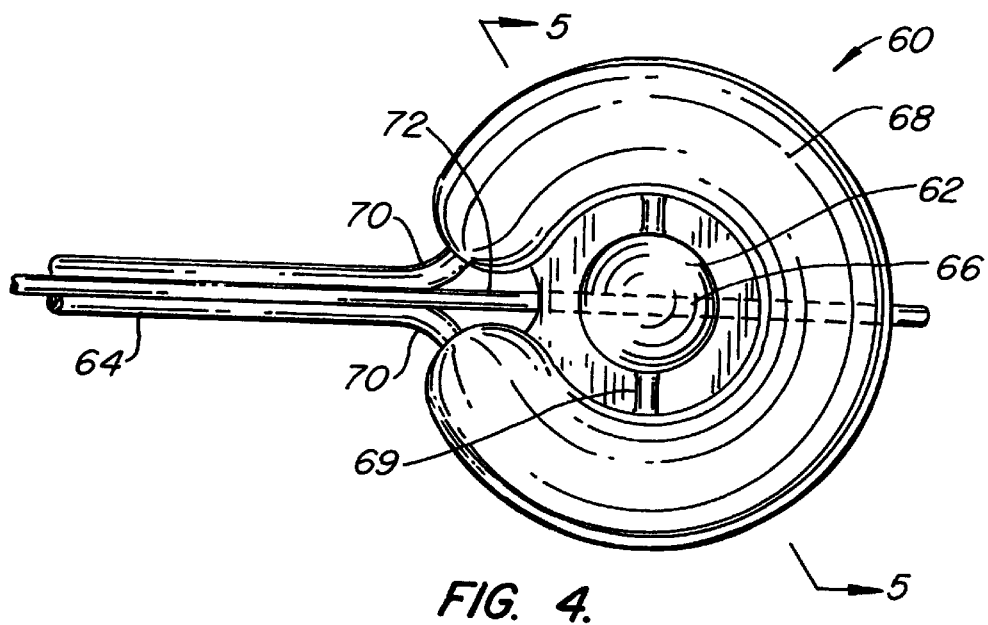
FIG. 4 is a top plan view of a spherical balloon having a cylindrical ring surrounding the balloon.
Figure 5:
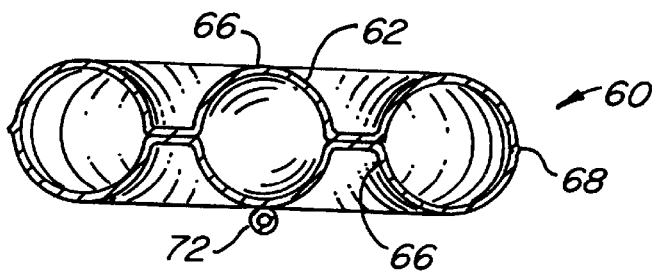
FIG. 5 is a vertical section through the spherical balloon and ring of FIG. 4.

The second embodiment of the inflatable device of the present invention is broadly denoted by the numeral 60 and is shown in FIGS. 4 and 5. Balloon 60 includes a central spherical part 62 which is hollow and which receives an inflating liquid under pressure through a tube 64. The spherical part is provided with a spherical outer surface 66 and has an outer periphery which is surrounded substantially by a ring shaped part 68 having tube segments 70 for inflation of part 68. A pair of passages 69 interconnect parts 62 and 68. A suction tube segment 72 draws liquid and debris from the bone cavity being formed by the balloon 60.

Provision can be made for a balloon sleeve 71 for balloon 60 and for all balloons disclosed herein. A balloon sleeve 71

(FIG. 9) is displaceably mounted in an outer tube 71a and can be used to insert the balloon 60 when deflated into a cortical bone. The sleeve 71 has resilient fingers 71b which bear against the interior of the entrance opening 71c of the vertebral bone 22 (FIG. 9A) to prevent tearing of the balloon. Upon removal of the balloon sleeve, liquid under pressure will be directed into tube 64 which will inflate parts 62 and 68 so as to compact the bone marrow within the cortical bone. Following this, balloon 60 is deflated and removed from the bone cavity.

FIGS. 6 and 6A show several views of a modified doughnut shape balloon 80 of the type shown in FIGS. 1 and 2, except the doughnut shapes of balloon 80 are not stitched onto one another. In FIG. 6, balloon 80 has a pear-shaped outer convex surface 82 which is made up of a first hollow part 84 and a second hollow part 85. A tube 88 is provided for directing liquid into the two parts along branches 90 and 92 to inflate the parts after the parts have been inserted into the medullary cavity of a bone. A catheter tube 16 is inserted into the space 96 between two parts of the balloon 80. An adhesive bonds the two parts 84 and 85 together at the interface thereof.

FIG. 6A shows the way in which the catheter tube 16 is inserted into the space or opening 96 between the two parts of the balloon 80.

FIG. 7 shows tube 88 of which, after directing inflating liquid into the balloon 80, can inject contrast material into the balloon 80 so that x-rays can be taken of the balloon with the inflating material therewithin to determine the proper placement of the balloon. Tube 16 is also shown in FIG. 6, it being attached in some suitable manner to the outer side wall surface of tube 88.

Figure 3:
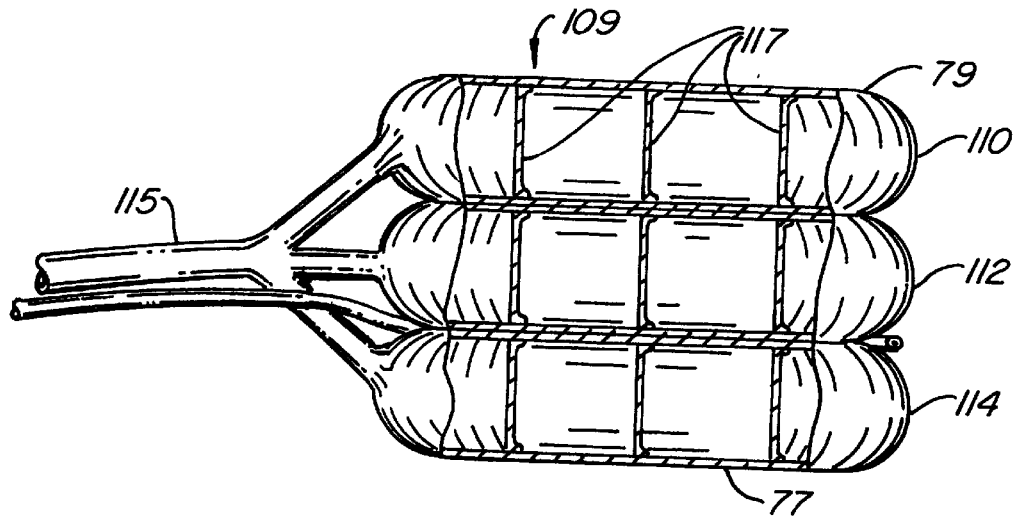
FIG. 3 is a schematic view of another embodiment of the balloon of the present invention showing three stacked balloons and string-like restraints for limiting the expansion of the balloon in directions of inflation.

Still another embodiment of the invention is shown in FIG. 3 which is similar to FIG. 1 except that it is round and not a doughnut and includes an inflatable device 109 having three balloon units 110, 112 and 114 which are inflatable and which have string-like restraints 117 which limit the expansion of the balloon units in a direction transverse to the longitudinal axes of the balloon units. The restraints are made of the same or similar material as that of the balloon so that they have some resilience but substantially no expansion capability.

A tube system 115 is provided to direct liquid under pressure into balloon units 110, 112 and 114 so that liquid can be used to inflate the balloon units when placed inside the bone in a deflated state. Following the proper inflation and compaction of the bone marrow, the balloon can be removed by deflating it and pulling it outwardly of the bone being treated. The restraints keep the opposed sides 77 and 79 substantially flat and parallel with each other.

In FIG. 10, another embodiment of the inflatable balloon is shown. The device is a kidney shaped balloon body 130 having a pair of opposed kidney shaped side walls 132 which are adapted to be collapsed and to cooperate with a continuous end wall 134 so that the balloon 130 can be forced into a bone 136 shown in FIG. 11. A tube 138 is used to direct inflating liquid into the balloon to inflate the balloon and cause it to assume the dimensions and location shown vertebral body 136 in FIG. 11. Device 130 will compress the cancellous bone if there is no fracture or collapse of the cancellous bone. The restraints for this action are due to the side and end walls of the balloon.

Figure 12:
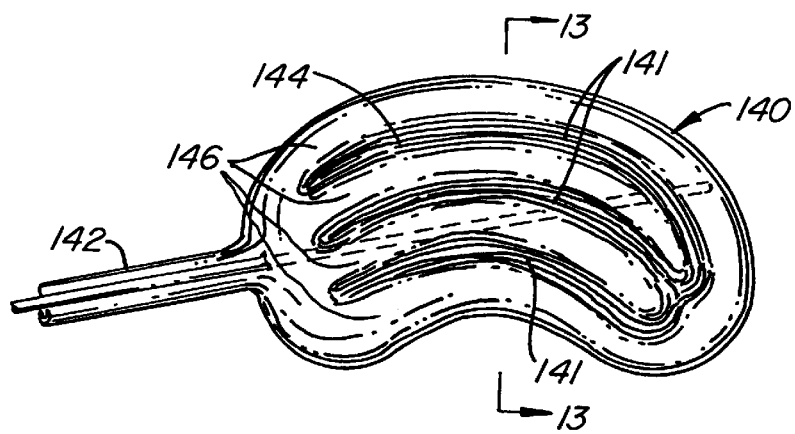
FIG. 12 is a top view of a kidney shaped balloon formed of several compartments by a heating element or branding tool.
Figure 13:
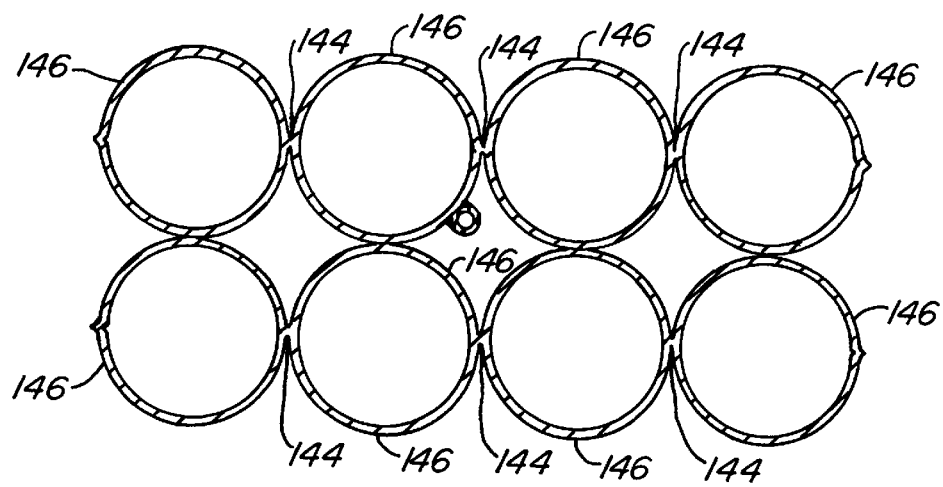
FIG. 13 is a cross-sectional view taken along line 13—13 of FIG. 12 but with two kidney shaped balloons that have been stacked.

FIG. 12 shows a balloon 140 which is also kidney shaped and has a tube 142 for directing an inflatable liquid into the tube for inflating the balloon. The balloon is initially a single chamber bladder but the bladder can be branded along curved lines or strips 141 to form attachment lines 144 which take the shape of side-by-side compartments 146 which are kidney shaped as shown in FIG. 13. A similar pattern of strips as in 140 but in straight lines would be applied to a balloon that is square or rectangular. The branding causes a welding of the two sides of the bladder to occur since the material is standard medical balloon material, which is similar to plastic and can be formed by heat.

Figure 14:
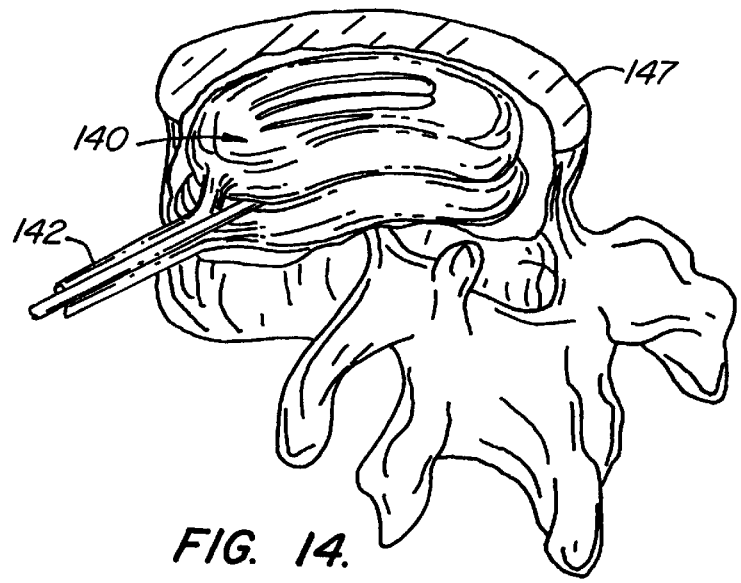
FIG. 14 is a view similar to FIG. 11 but showing the stacked kidney shaped balloon of FIG. 13 in the vertebral bone.

FIG. 14 is a perspective view of a vertebral body 147 containing the balloon of FIG. 12, showing a double stacked balloon 140 when it is inserted in vertebral bone 147.

Figure 15:
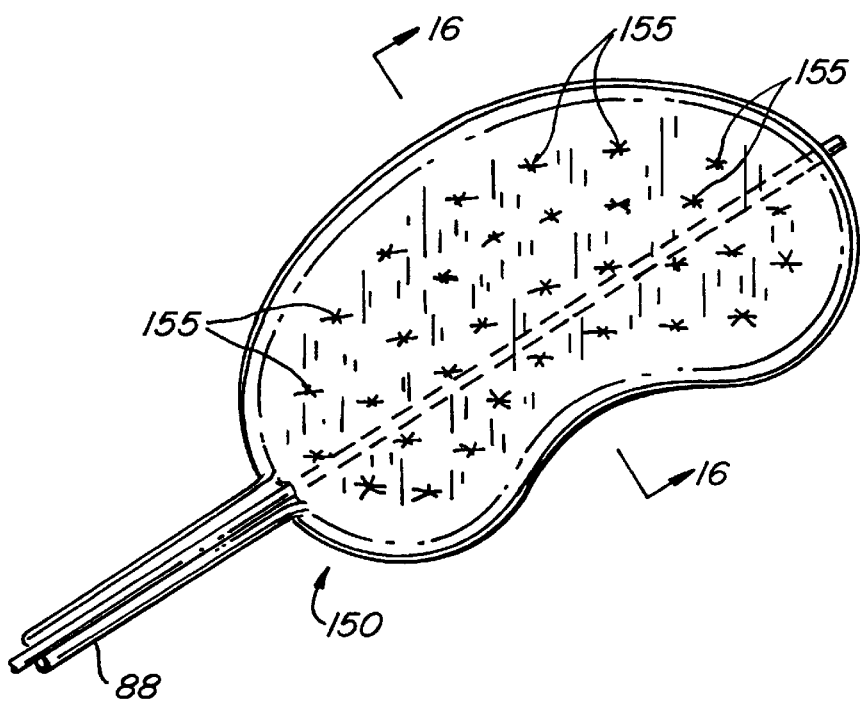
FIG. 15 is a top view of a kidney balloon showing outer tufts holding inner strings in place interconnecting the top and bottom walls of the balloon.
Figure 16:
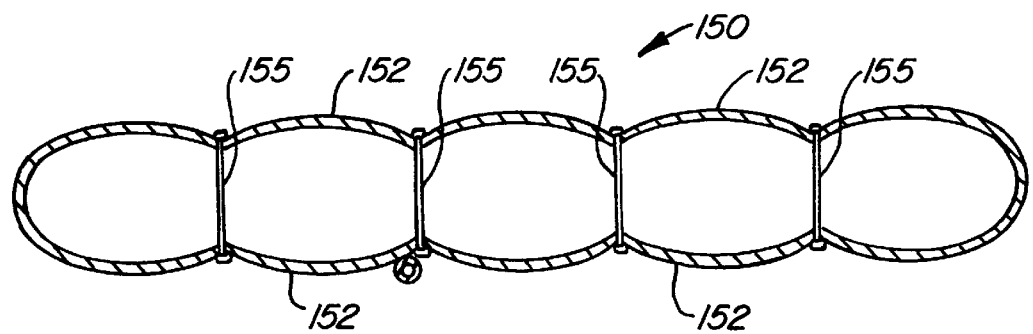
FIG. 16 is a cross sectional view taken along lines 16—16 of FIG. 15.

FIG. 15 is a view similar to FIG. 10 except that tufts 155, which are string-like restraints, extend between and are connected to the side walls 152 of inflatable device 150 and limit the expansion of the side walls with respect to each other, thus rendering the side walls generally parallel with each other. Tube 88 is used to fill the kidney shaped balloon with an inflating liquid in the manner described above.

The dimensions for the vertebral body balloon will vary across a broad range. The heights (H, FIG. 11) of the vertebral body balloon for both lumbar and thoracic vertebral bodies typically range from 0.5 cm to 3.5 cm. The anterior to posterior (A, FIG. 11) vertebral body balloon dimensions for both lumbar and thoracic vertebral bodies range from 0.5 cm to 3.5 cm. The side to side (L, FIG. 11) vertebral body dimensions for thoracic vertebral bodies will range from 0.5 cm to 3.5 cm. The side to side vertebral body dimensions for lumbar vertebral bodies will range from 0.5 cm to 5.0 cm. An optimal vertebral body balloon is stacked with two or more members of unequal height where each member can be separately inflated through independent tube systems. The total height of the stack when fully inflated should be within the height ranges specified above. Such a design allows the fractured vertebral body to be returned to its original height in steps, which can be easier on the surrounding tissue, and it also allows the same balloon to be used in a wider range of vertebral body sizes.

The eventual selection of the appropriate balloon for, for instance, a given vertebral body is based upon several factors. The anterior-posterior (A-P) balloon dimension for a given vertebral body is selected from the CT scan or plain film x-ray views of the vertebral body. The A-P dimension is measured from the internal cortical wall of the anterior cortex to the internal cortical wall of the posterior cortex of the vertebral body. In general, the appropriate A-P balloon dimension is 5 to 7 millimeters less than this measurement.

The appropriate side to side balloon dimensions for a given vertebral body is selected from the CT scan or from a plain film x-ray view of the vertebral body to be treated. The side to side distance is measured from the internal cortical walls of the side of the vertebral bone. In general, the appropriate side to side balloon dimension is 5 to 7 millimeters less than this measurement by the addition of the lumbar vertebral body tends to be much wider than side to side dimension then their A-P dimension. In thoracic vertebral bodies, the side to side dimension and their A-P dimensions are almost equal.

The height dimensions of the appropriate vertebral body balloon for a given vertebral body is chosen by the CT scan or x-ray views of the vertebral bodies above and below the vertebral body to be treated. The height of the vertebral bodies above and below the vertebral body to be treated are measured and averaged. This average is used to determine the appropriate height dimension of the chosen vertebral body balloon.

Balloons For Long Bones

Long bones which can be treated with the use of balloons of the present invention include distal radius (larger arm bone at the wrist), proximal tibial plateau (leg bone just below the knee), proximal humerus (upper end of the arm at the shoulder), and proximal femoral head (leg bone in the hip).

Distal Radius Balloon

For the distal radius, a balloon 160 is shown in the distal radius 152 and the balloon has a shape which approximates a pyramid but more closely can be considered the shape of a humpbacked banana in that it substantially fills the interior of the space of the distal radius to force cancellous bone 154 lightly against the inner surface 156 of cortical bone 158. Note that the spherical radius balloon discussed above may also be appropriately sized for the distal radius 152.

Figure 17A:
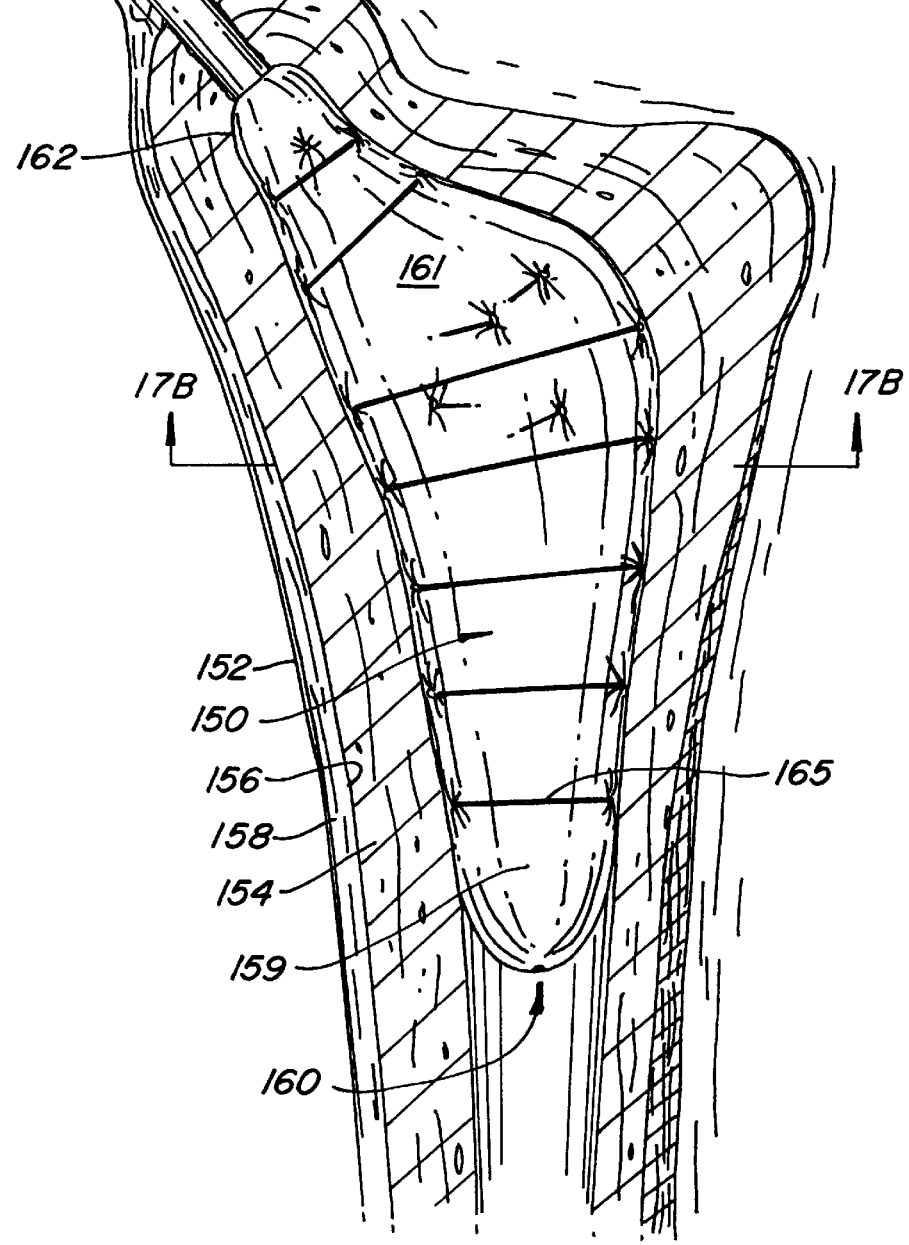
FIG. 17A is a dorsal view of a humpback banana balloon in a right distal radius.
Figure 17B:
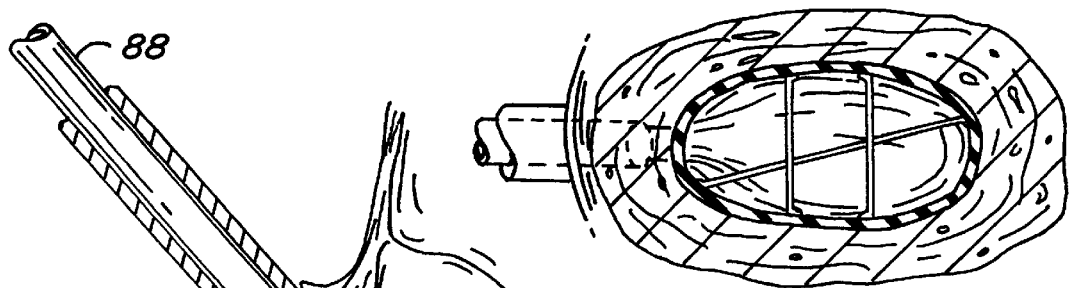
FIGS. 17B is a cross sectional view of FIG. 17A taken along line 17B—17B of FIG. 17A.

The balloon 160 has a lower, conical portion 159 which extends downwardly into the hollow space of the distal radius 152, and this conical portion 159 increases in cross section as a central distal portion 161 is approached. The cross section of the balloon 160 is shown at a central location (FIG. 17B) and this location is near the widest location of the balloon. The upper end of the balloon, denoted by the numeral 162, converges to the catheter 88 for directing a liquid into the balloon for inflating the same to force the cancellous bone against the inner surface of the cortical bone. The shape of the balloon 160 is determined and restrained by tufts formed by string restraints 165. These restraints are optional and provide additional strength to the balloon body 160, but are not required to achieve the desired configuration. The balloon is placed into and taken out of the distal radius in the same manner as that described above with respect to the vertebral bone.

The dimensions of the distal radius balloon vary as follows:

The proximal end of the balloon (i.e. the part nearest the elbow) is cylindrical in shape and will vary from 0.5×0.5 cm to 1.8×1.8 cm.

The length of the distal radius balloon will vary from 1.0 cm to 12.0 cm.

The widest medial to lateral dimension of the distal radius balloon, which occurs at or near the distal radio-ulnar joint, will measure from 1.0 cm to 2.5 cm.

The distal anterior-posterior dimension of the distal radius balloon will vary from 0.5 to 3.0 cm.

Proximal Humerus Fracture Balloon

The selection of the appropriate balloon size to treat a given fracture of the distal radius will depend on the radiological size of the distal radius and the location of the fracture.

Figure 18:
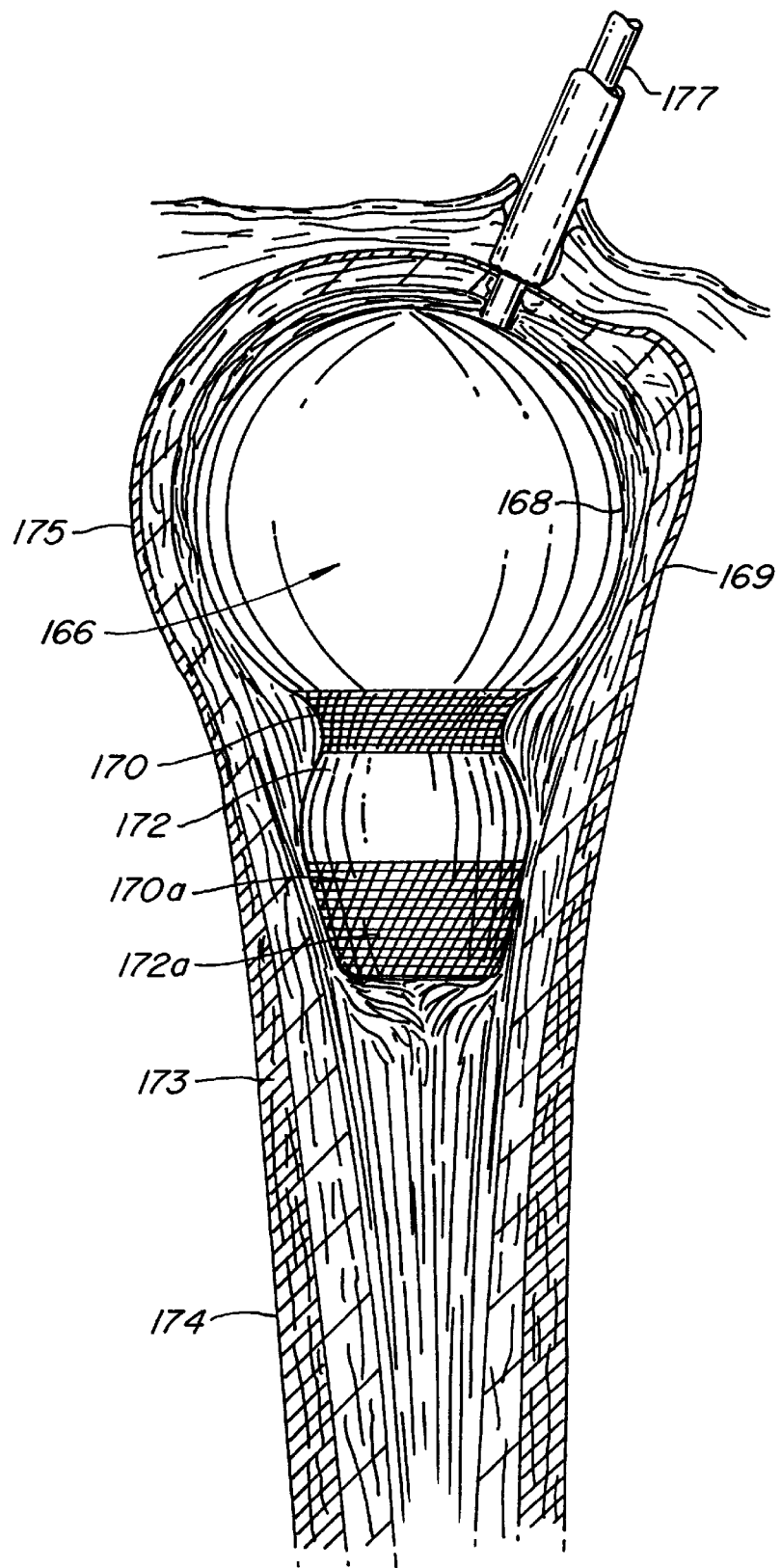
FIG. 18 is a spherical balloon with a base in a proximal humerus viewed from the front (anterior) of the left proximal humerus.

In the case of the proximal humerus 169, a balloon 166 shown in FIG. 18 is spherical and has a base design. It compacts the cancellous bone 168 in a proximal humerus 169. A mesh 170, embedded or laminated and/or winding, may be used to form a neck 172 on the balloon 166, and second mesh 170a may be used to conform the bottom of the base 172a to the shape of the inner cortical wall at the start of the shaft. These restraints provide additional strength to the balloon body, but the configuration can be achieved through molding of the balloon body. This is so that the cancellous bone will be as shown in the compacted region surrounding the balloon 166 as shown in FIG. 18. The cortical bone 173 is relatively wide at the base 174 and is thin-walled at the upper end 175. The balloon 166 has a feed tube 177 into which liquid under pressure is forced into the balloon to inflate it to lightly compact the cancellous bone in the proximal humerus. The balloon is inserted into and taken out of the proximal humerus in the same manner as that described above with respect to the vertebral bone.

The dimensions of the proximal humerus fracture balloon vary as follows:

The spherical end of the balloon will vary from 1.0×1.0 cm to 3.0×3.0 cm.

The neck of the proximal humeral fracture balloon will vary from 0.8×0.8 cm to 3.0×3.0 cm.

The width of the base portion or distal portion of the proximal numeral fracture balloon will vary from 0.5×0.5 cm to 2.5×2.5 cm.

The length of the balloon will vary from 4.0 cm to 14.0 cm.

The selection of the appropriate balloon to treat a given proximal humeral fracture depends on the radiologic size of the proximal humerus and the location of the fracture.

Figure 18A:
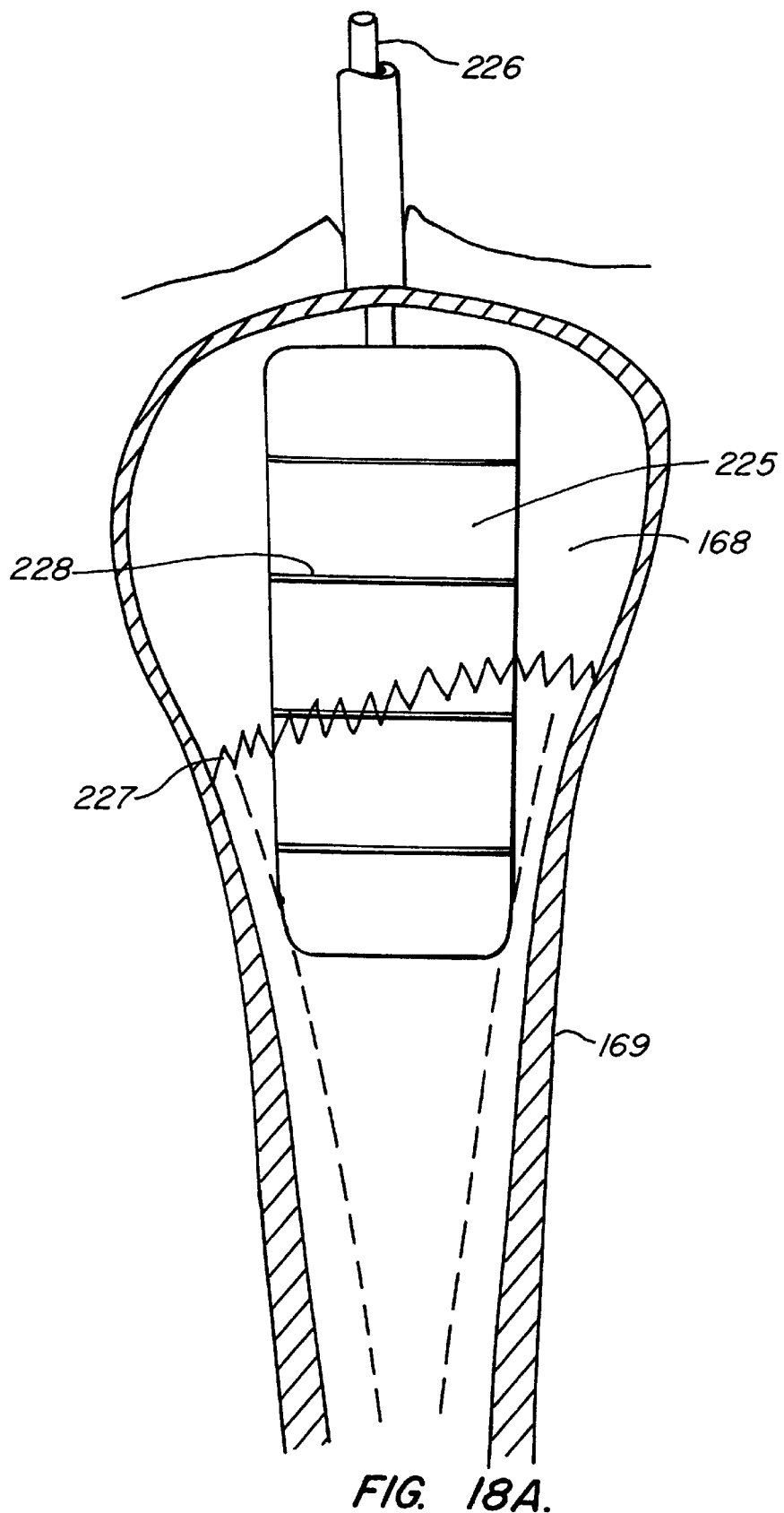
FIG. 18A is a cylindrical balloon viewed from the front (anterior) of the left proximal humerus.

Another balloon adapted for use in the proximal humerus 169 is the cylindrical balloon 225 shown in FIG. 18A. Like the feed tube 177 of FIG. 18, cylindrical balloon 225 has an inflation tube 226 for inserting liquid therein. 227 shows the site of a typical shoulder fracture. The cylinder can have a uniform circumference or it can be wider at one end than at the other. The wider end would be attached to the inflating tube 226 to compact the cancellous bone 168 of the humeral head 168a. Appropriate restraints to maintain the shape include multiple inelastic bands (228 is one of them) spaced around the circumference at regular intervals. For a cylinder with a uniform width, the restraining bands will usually have the same diameter. For a cylinder with one end wider than the other, each band would successively have a wider diameter.

The length of the balloon is usually the same as that of the sphere on the base, preferably ranging from 4–14 cm, with the width usually ranging from 0.5 cm to 2.5 cm. The surgeon uses plain film X-ray of the humerus to be treated. The required length is defined by measuring the distance from the inner humeral head at the site of insertion to about 3 cm below the site of fracture. The diameter is at least 0.5 cm smaller than the inner diameter of the cortex of the humeral shaft (at its narrowest point along the balloon's length).

Proximal Tibial Plateau Fracture Balloon

Figure 19A:
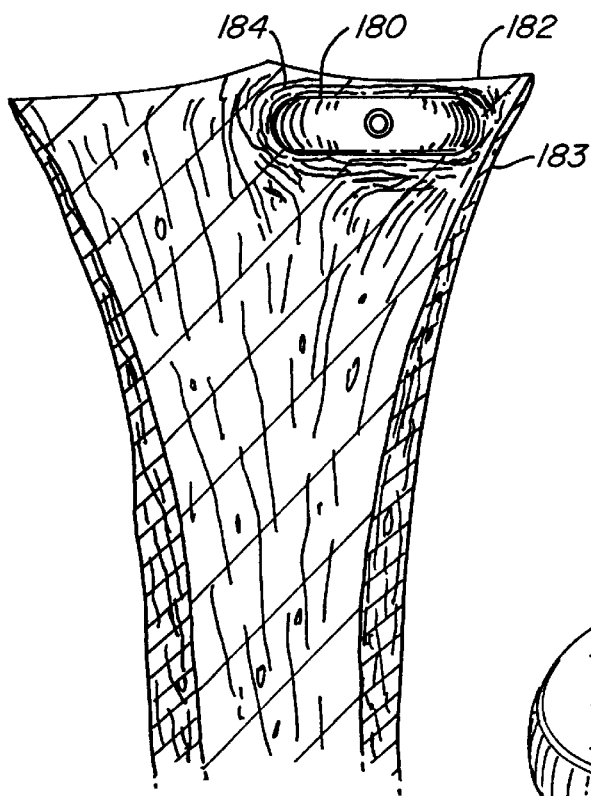
FIG. 19A is the front (anterior) view of the proximal tibia with the elliptical cylinder balloon introduced beneath the medial tibial plateau.
Figure 19B:
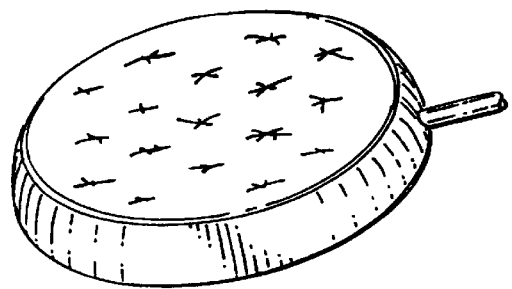
FIG. 19B is a three quarter view of the balloon of FIG. 19A.
Figure 19C:
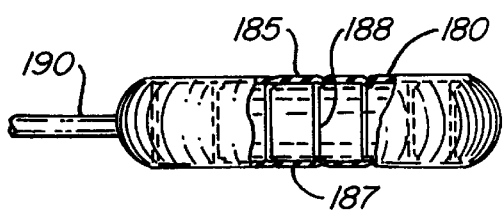
FIG. 19C is a side elevational view of the balloon of FIG. 19A.
Figure 19D:
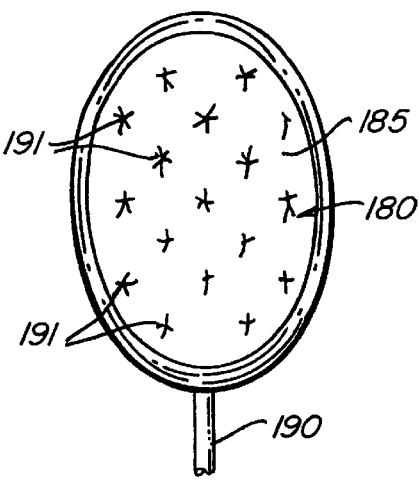
FIG. 19D is a top plan view of the balloon of FIG. 19A.

The tibial fracture is shown in FIG. 19A in which a balloon 180 is placed in one side 182 of a tibia 183. The balloon, when inflated, compacts the cancellous bone in the layer 184 surrounding the balloon 180. A cross section of the balloon is shown in FIG. 19C wherein the balloon has a pair of opposed sides 185 and 187 which are interconnected by restraints 188 which can be in the form of strings or flexible members of any suitable construction. The main purpose of the restraints is to make the sides 185 and 187 substantially parallel with each other and non-spherical. A tube 190 is coupled to the balloon 180 to direct liquid into and out of the balloon. The ends of the restraints are shown in FIGS. 19B and 19D and denoted by the numeral 191. The balloon is inserted into and taken out of the tibia in the same manner as that described above with respect to the vertebral bone. FIG. 19B shows a substantially circular configuration for the balloon; whereas, FIG. 19D shows a substantially elliptical version of the balloon.

The dimensions of the proximal tibial plateau fracture balloon vary as follows:

The thickness or height of the balloon will vary from 0.5 cm to 5.0 cm.

The anterior/posterior (front to back) dimension will vary from 1.0 cm to 6.0 cm.

The side to side (medial to lateral) dimension will vary from 1.0 cm to 6.0 cm.

The selection of the appropriate balloon to treat a given tibial plateau fracture will depend on the radiological size of the proximal tibial and the location of the fracture.

Femoral Head Balloon

Figures 20, 20A:
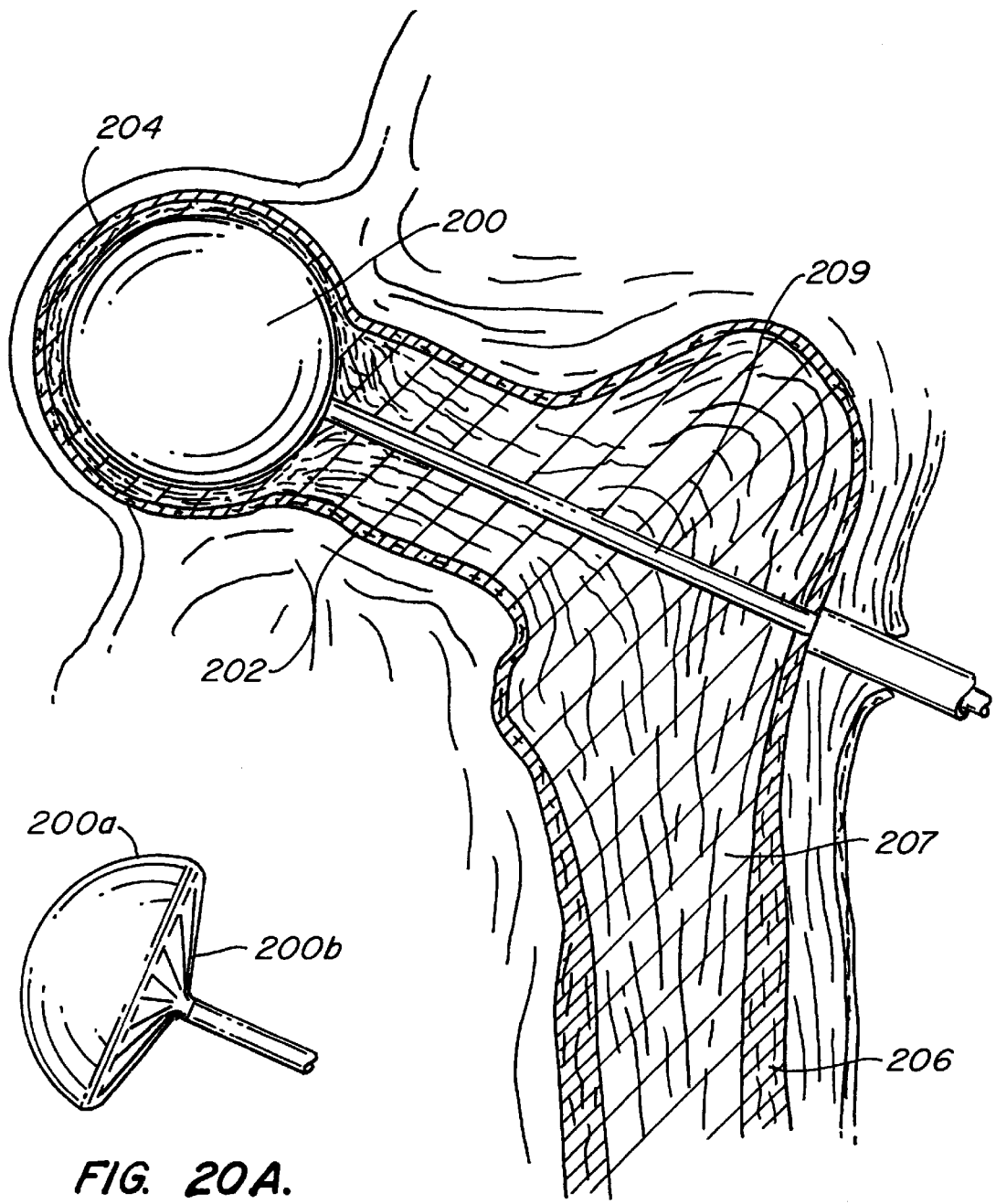
FIG. 20 is a spherically shaped balloon for treating avascular necrosis of the head of the femur (or humerus) as seen from the front (anterior) of the left hip.
FIG. 20A is a side view of a hemispherically shaped balloon for treating avascular necrosis of the head of the femur (or humerus)

In the case of the femoral head, a balloon 200 is shown as having been inserted inside the cortical bone 202 of the femoral head which is thin at the outer end 204 of the femur and which can increase in thickness at the lower end 206 of the femur. The cortical bone surrounds the cancellous bone 207 and this bone is compacted by the inflation of balloon 200. The tube for directing liquid for inflation purposes into the balloon is denoted by the numeral 209. It extends along the femoral neck and is directed into the femoral head which is generally spherical in configuration. FIG. 20A shows that the balloon, denoted by the numeral 200a, can be hemispherical as well as spherical, as shown in FIG. 20. The balloon 200 is inserted into and taken out of the femoral head in the same manner as that described with respect to the vertebral bone. The hemispherical shape is maintained in this example by bonding overlapping portions of the bottom, creating pleats 200b as shown in FIG. 20A.

The dimensions of the femoral head balloon vary as follows:

The diameter of the femoral head balloon will vary from 1.0 cm to up to 4.5 cm. The appropriate size of the femoral head balloon to be chosen depends on the radiological or CT scan size of the head of the femur and the location and size of the avascular necrotic bone. The dimensions of the hemispherical balloon are the same as the those of the spherical balloon, except that approximately one half is provided.

Prevention of Hip Fracture

Figure 21:
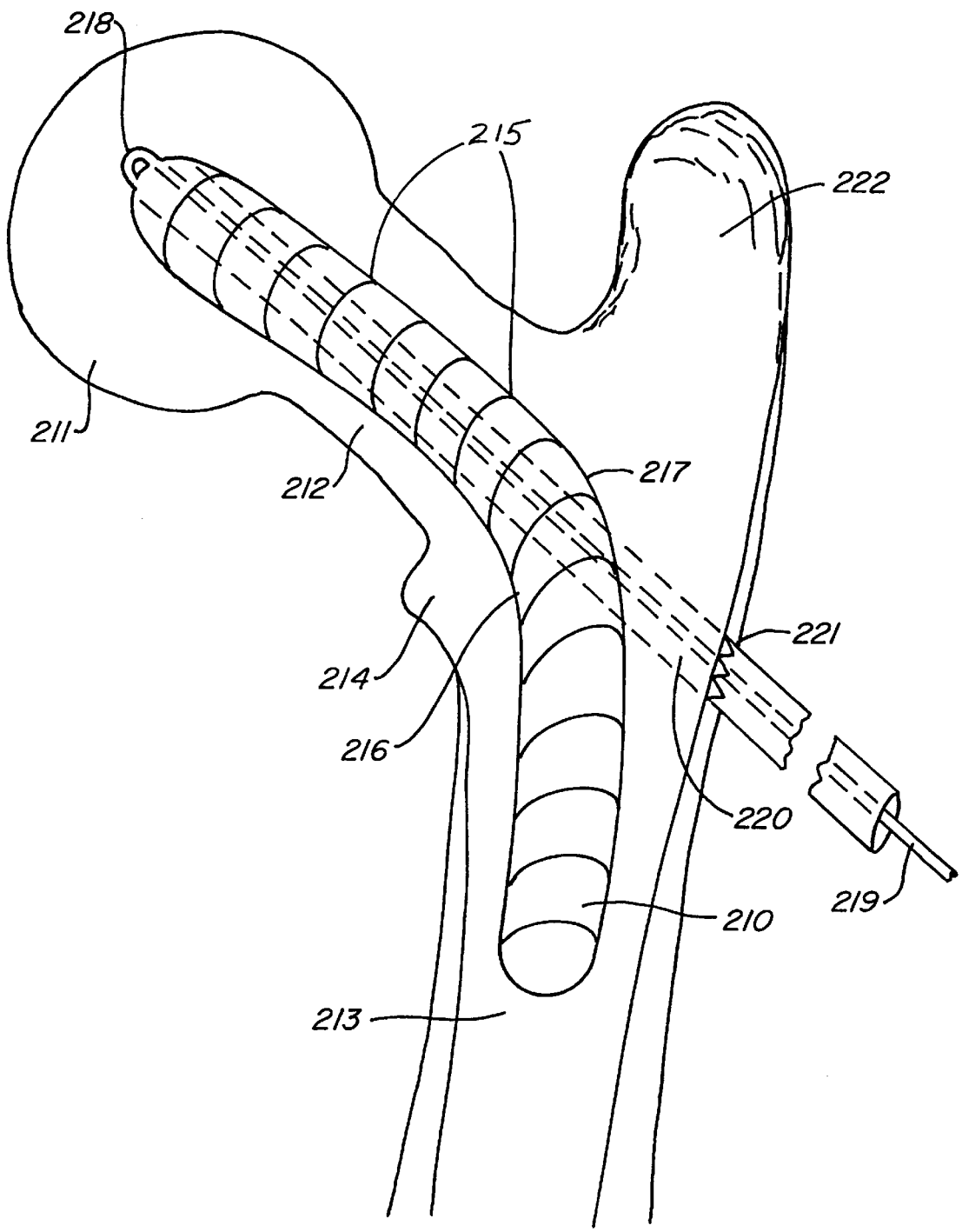
FIG. 21 is a balloon for preventing hip fracture as seen from the front (anterior) of the left hip.

FIG. 21 illustrates a "boomerang" balloon 210 adapted for preventing hip fracture. When inflated, the "boomerang" balloon 210 is a cylinder which gradually bends in the middle, like a boomerang, and extends from about 0.5 cm from the end of the femoral head 211 through the femoral neck 212 and down into the proximal femoral diaphysis 213 about 5–7 cm past the lesser trochanter 214. Balloon 210 preferably maintains its shape by rings of inelastic material (215 is one of them) held closer together on one side by attachment to a shorter inelastic band 216 running the length of the side of balloon and further apart by attachment to a longer inelastic band 217 bonded on the opposite side.

After and prior to inflation, balloon 210 is folded back (shown in dotted lines at 218) against the inflation tube 219. Prior to inflation, the balloon 210 is also rolled up and held against the inflation tube with loose attachments that break when the balloon is inflated. To insert the balloon on its inflation tube into the hip, the surgeon uses a power drill under radiographic guidance to create a cavity 220 that is usually 4–6 mm wide starting at the lateral femoral cortex 221 and proceeding into the femoral head 211. Inflation of balloon 210 into the greater trochanteric region 222 instead of down the femoral diaphysis 213 is not desirable and is prevented by the shape of the balloon, by its placement and correct orientation (the deflated balloon facing the lesser trochanter). After the balloon 210 has been inflated within the cavity 220 (see the dotted lines in FIG. 21), the predetermined size and shape of the balloon biases the proximal portion of the balloon downward into the lesser trochanter. Optionally, a second cavity can be drilled down into the diaphysis, starting from the same entry point or from the other side.

Patients with bone density in the hip below a threshold value are at increased risk of hip fracture, and lower densities create greater risk. Patient selection is done through a bone density scan. The balloon length is chosen by the surgeon to extend about 0.5 cm from the end of the femoral head, through the femoral neck and into the proximal femoral diaphysis, usually about 4–8 cm below the lesser trochanter. The balloon diameter is chosen by measuring the inner cortical diameter of the femoral neck (the most narrow area) and subtracting 0.5 cm. The preferred dimensions of the "boomerang balloon" are a total length of 10–20 cm and a diameter of about 1.0–2.5 cm. (A "humpback banana" balloon with appropriate length may also be useful in hip fracture prevention, as long as the "humpback" width does not exceed the allowed femoral neck dimensions.)

Patients having the lowest bone densities in the femoral head may require greater compacting in the femoral head, which may, for example, be provided by using two balloons, one after the other: the "boomerang" followed by the femoral head balloon (inserted at the same point and expanded prior to inserting any supporting material.) Alternatively, the "boomerang" balloon may be adapted to have a distal portion that approximates the shape of the femoral head balloon.

Other Uses, Methods And Balloons

The cavity created by the balloon can be filled with a medically-appropriate formulation of a drug or a growth factor. As an example of delivering a drug, a typical dose of the antibiotic, gentamicin, to treat a local osteomyelitis (bone infection), is 1 gram (although the therapeutic range for gentamicin is far greater, from 1 nanogram to 100 grams, depending on the condition being treated and the size of the area to be covered). A medically-suitable gel formulated with appropriate gel materials, such as polyethylene glycol, can contain 1 gram of gentamicin in a set volume of gel, such as 10 cc. A balloon with this volume whose shape and size is appropriate for the site being treated (that is, the balloon cannot move and thereby break the cortical bone when inflated at the chosen site) can be used to compact the infected cancellous bone. This creates a space which can be filled with the antibiotic gel in an open or minimally invasive procedure. This places and holds the required amount of drug right at the site needing treatment, and protects the drug from being washed away by blood or other fluids. Not only can the dose be optimized, but additional doses can be applied at later times without open surgery, enhancing the therapeutic outcome. If the required cavity for the optimal drug dose weakens the bone, the bone can be protected from future fracture with a cast or with current internal or external metal or plastic fixation devices. The therapeutic substance put into bone may be acting outside the bone as well. A formulation containing chemotherapeutic agent could be used to treat local solid tumors, localized multiple myeloma or even a nearby osteosarcoma or other tumor near that bone.

As an alternative, to deliver therapeutic substances, balloons can be dipped in a medical formulation (often a dry powder, liquid or gel) containing a medically-effective amount of any desired antibiotic, bone growth factor or other therapeutic agent to coat the balloon with the above-mentioned substance before it is inserted into a bone being treated. Optionally, the balloon can be wholly or partially inflated with air or liquid before the coating is performed. Optionally, the coated balloon can be dried with air or by other means when the applied formulation is wet, such as a liquid or a gel. The balloon is refolded as required and either used immediately or stored, if appropriate and desired. Coated on the balloon, therapeutic substances can be delivered while cancellous bone is being compressed, or with an additional balloon once the cavity is made.

The methods described above can also be used to coat Gelfoam or other agents onto the balloon before use. Inflating the Gelfoam-coated balloon inside bone will further fill any cracks in fractured bone not already filled by the compressed cancellous bone.

FIGS. 22A–C schematically illustrate one system and method for delivering a therapeutic substance to the bone according to the present invention. As shown in FIG. 22A, an inflated balloon 229 attached to an inflating tube 230 is stabilized with a clip 231 that couples tube 230 to a wire 232. As shown in FIG. 22B, a measured amount of gel formulation containing the desired amount of substance 233 is uniformly dispensed from a container 234, preferably in thin lines 235, onto the outer surface of a balloon 236. As shown in FIG. 22C, the coated balloon 237 is then deflated and allowed to dry until the get sets. The coated balloon 237 is then ready for packaging for use by the surgeon. Of course, the balloon can also be coated without prior inflation. In addition, the coating substance can be the desired compound alone in its natural state (solid, liquid or gas) or in an appropriate formulation, including a dry powder, an aerosol or a solution. The optional drying time will, of course, depend on the nature of the compound and its formulation.

Delivering a therapeutic substance on the outside of the balloon used to compact the bone or with a second (slightly larger) balloon after the bone is compacted, is qualitatively different than putting formulated drug into the cavity. When delivered while compressing the bone, the substance becomes incorporated into the compacted bone. This can serve as a way to instantly formulate a slow release version of the substance. It simultaneously allows the surgeon to fill the cavity with an appropriate supporting material, like acrylic bone cement or biocompatible bone substitute, so no casting or metal fixation is required. Such a combination allows the surgeon, for example, to percutaneously fix an osteoporotic fracture while delivering a desired therapeutic substance (like an antibiotic, bone growth factor or osteoporosis drug) to the site. Thus, casts or metal fixation devices are generally not ever required.

Medically-effective amounts of therapeutic substances are defined by their manufacturers or sponsors and are generally in the range of 10 nanograms to 50 milligrams per site, although more or less may be required in a specific case. Typical antibiotics include gentamicin and tobramycin. Typical bone growth factors are members of the Bone Morphogenetic Factor, Osteogenic Protein, Fibroblast Growth Factor, Insulin-Like Growth Factor and Transforming Growth Factor alpha and beta families. Chemotherapeutic and related agents include compounds such as cisplatin, doxorubicin, daunorubicin, methotrexate, taxol and tamoxifen. Osteoporosis drugs include estrogen, calcitonin, diphosphonates, and parathyroid hormone antagonists.

The balloons described in this invention can be used in open surgical procedures at the sites discussed above to provide an improved space for inserting orthopedic implants, bone graft, bone substitutes, bone fillers or therapeutic substances. The size and shape of balloon chosen would be determined by the site being treated and then by the size, shape or amount of material that the surgeon wants to insert into the remaining bone. Square and rectangular balloons can be used at any site for the placement of bone substitutes like hydroxyapatites which are available in those shapes. Balloons would be made to match those predetermined sizes, and the surgeon would chose the balloon to fit the size of material chosen.

To insert materials which do not flow into the balloon-made cavity, like hydroxyapatite granules or bone mineral matrix, the surgeon can push them down a tube with a long pin whose diameter is slightly more narrow than the inner diameter of the canula through procedures which the minimally-invasive procedure is taking place. During open surgery, the surgeon can approach the bone to be treated as if the procedure is percutaneous, except that there is no skin and other tissues between the surgeon and the bone being treated. This keeps the cortical bone as intact as possible. If the material to be inserted does not flow and should not be pushed into the cavity through a canula (as in the case of the hydroxyapatite block, because that can cause damage), the surgeon can make the cavity using the "minimally invasive" approach, then punch a hole using standard tools (such as a punch, gouge or rasp) into one side of the cortical bone to allow insertion of the block. This same approach can be used for implanting a metal prosthesis, such as the metal tibial component of a total knee replacement system.

Different sizes and/or shapes of balloons may be used at sites not specified above, such as the jaw bones, the midshaft of the arm and leg bones, the cervical vertebral bodies, the foot and ankle bones, the ribs and the like. One of the keys to choosing balloon shape and size in treating or preventing bone fracture is the teaching of this application that, optimally, about 70–90% of the cancellous bone needs to be compacted in cases where the bone disease causing fracture (or the risk of fracture) is the loss of cancellous bone mass (as in osteoporosis). Compacting less than the optimal 70–90% of the cancellous bone at the site being treated (or 40–99% as the workable range) may leave too much of the diseased cancellous bone at the treated site. The diseased cancellous bone remains weak and can later collapse, causing fracture despite treatment. With this principle, the allowed shapes and minimum sizes for any chosen bone are explained and defined.

There are specific exceptions to the 70–90% rule, as described in this specification. One is when the bone disease being treated is localized, as in avascular necrosis, where local loss of blood supply is killing bone in a limited area. In that case, the balloons can be smaller, because the diseased area requiring treatment is smaller. A second exception is in the use of the devices to improve insertion of solid materials in defined shapes, like hydroxyapatite and components in total joint replacement. In these cases, the balloon shape and size is defined by the shape and size of the material being inserted. Another exception is the delivery of therapeutic substances. In this case, the cancellous bone may or may not be affected. If it is not, it is being sacrificed by compacting it to improve the delivery of a drug or growth factor which has an important therapeutic purpose. In this case, the bone with the drug inside is supported while the drug works and then the bone heals through casting or current fixation devices.

Another key to choosing balloon shape and size is the teaching of this invention that inelastic balloon restraints are generally required and that inelastic balloon materials are preferred. These materials safely and easily prevent the balloon from expanding beyond its predetermined shape and size which is defined by the limits of the normal dimensions of the outside edge of the cancellous bone (which is the inside of the cortical bone). A balloon which is too big, for example, creates the risk of immediate fracture, so this defines the upper limits of balloon sizes at each site. With many typical angioplasty balloons, surgeons usually rely on monitoring pressure (instead of the balloon design features of this invention) to prevent their balloons from inflating too much. This requires greater surgical skill than the teachings of this application, which are to take an X-ray of the site to be treated and measure the important dimensions as described herein. In addition, in bone treatment, relying on pressure can result in an inferior clinical outcome. The surgeon generally will not know in advance what pressure is required to completely compact the cancellous bone, because this varies depending on the thickness of the cancellous bone and the extent to which it has lost density due to its disease. The surgeon is likely to underinflate the balloon to avoid the harsh consequences of overinflation and immediate fracture. This leaves too much cancellous bone and can lead to future fracture.

Another teaching of this application is that it requires maximal pressures equally exerted in all directions to compress cancellous bone. This is an inherent property of the balloons drawn in figures in this application and all the others described in the specification. If the balloon design does not allow this, it usually will not compress cancellous bone. The shape of the cancellous bone to be compressed, and the local structures that could be harmed if bone were moved inappropriately, are generally understood by medical professionals using textbooks of human skeletal anatomy along with their knowledge of the site and its disease or injury. Ranges of shapes and dimensions are defined by the site to be treated. Precise dimensions for a given patient are determined by X-ray of the site to be treated, the therapeutic goal and safety constraints at the site. For diseased bone, replacement of the most of the cancellous bone is usually desired, so a balloon whose shape and size will compress around 70–90% of the volume of the cancellous bone in the treated region will be chosen. However, balloons that are smaller or larger may be appropriate, particularly where delivery of a therapeutic substance is the main goal. There, the balloon size could be chosen by the desired amount of therapeutic substance, keeping in mind that the balloon should not displace the cortical bone beyond its normal dimensions.

We claim:

1. A device for insertion into a hip bone having an interior volume occupied, at least in part, by cancellous bone, the device comprising a body having an axis and capable of expansion about the axis from a collapsed geometry, adapted for insertion into the interior volume, and an expanded geometry, adapted for compacting cancellous bone in the interior volume, a first essentially inelastic band extending along the axis, and a second essentially inelastic band extending along the axis spaced from the first essentially inelastic band, the first essentially inelastic band and the second essentially inelastic band having different axial lengths to restrain expansion such that the body bend along the axis during expansion.

2. A device according to claim 1
wherein the first and second essentially inelastic bands bias the body, when in the expanded geometry, toward a curved shape.

3. A device according to claim 1
wherein the first and second essentially inelastic bands are generally diametrically spaced along the axis.

4. A device according to claim 1
and further including at least one ring encircling the body about the axis and coupled to the first and second essentially inelastic bands.

5. A device according to claim 4
wherein the at least one ring comprises an essentially inelastic material.

6. A device according to claim 1
wherein the body comprises an essentially inelastic material.

7. A device according to claim 1
wherein the body comprises an essentially semi-elastic material.

8. A device according to claim 1
wherein the body comprises an essentially elastic material.

9. A device according to claim 1
and further including a catheter tube having a distal end, and wherein the distal end carries the body.

10. A device according to claim 1
and further including a source of therapeutic substance arranged for compaction by the body into cancellous bone compressed by the body.

* * * * *